US012661157B2

(12) United States Patent
Bootwala et al.

(10) Patent No.: US 12,661,157 B2
(45) Date of Patent: Jun. 23, 2026

(54) SPINAL CONNECTORS AND RELATED METHODS

(71) Applicant: DePuy Synthes Products, Inc., Raynham, MA (US)

(72) Inventors: Zoher Bootwala, Foxboro, MA (US); Michael Gorhan, Mansfield, MA (US); Adam LaWare, Medford, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 18/492,643

(22) Filed: Oct. 23, 2023

(65) Prior Publication Data

US 2024/0050133 A1     Feb. 15, 2024

Related U.S. Application Data

(63) Continuation of application No. 17/319,033, filed on May 12, 2021, now Pat. No. 11,813,000, which is a (Continued)

(51) Int. Cl.
*A61B 17/70* (2006.01)

(52) U.S. Cl.
CPC ...... *A61B 17/7049* (2013.01); *A61B 17/7011* (2013.01); *A61B 17/705* (2013.01)

(58) Field of Classification Search
CPC .................................................. A61B 17/7049
See application file for complete search history.

(56) References Cited

U.S. PATENT DOCUMENTS

| 5,645,544 | A | 7/1997 | Tai et al. |
| 6,551,318 | B1 | 4/2003 | Stahurski |

(Continued)

FOREIGN PATENT DOCUMENTS

| EP | 1690505 | B1 | 8/2008 |
| EP | 2465453 | B1 | 4/2015 |

(Continued)

OTHER PUBLICATIONS

[No Author Listed] Expedium. Universal Connector Set: Connecting you to solutions. DePuy Spine, Inc., a Johnson & Johnson Company, Product brochure, 2009, 2 pages.

(Continued)

*Primary Examiner* — Tessa M Matthews
(74) *Attorney, Agent, or Firm* — Barnes & Thornburg LLP

(57) ABSTRACT

In some embodiments, a connector can be configured to couple a first fixation element (e.g., a first rod) to a second fixation element (e.g., a second rod). One or both of the first and second fixation elements can be included with the connector, or one or both can be separately provided. In some instances, at least one of the fixation elements is previously implanted in a patient. The connector can provide one or more degrees of freedom between the first and second fixation elements. The connector can also include a locking element configured to (1) lock one or more of the fixation elements to the connector, and (2) lock one or more of the degrees of freedom between the fixation elements. The connector can be configured to snap onto or otherwise engage a fixation element in a manner that provides tactile and/or audible feedback to the surgeon.

23 Claims, 19 Drawing Sheets

Related U.S. Application Data continuation of application No. 15/634,022, filed on Jun. 27, 2017, now Pat. No. 11,020,151, which is a continuation of application No. 14/496,804, filed on Sep. 25, 2014, now Pat. No. 9,724,131.

(56) References Cited

U.S. PATENT DOCUMENTS

| | | | |
|---|---|---|---|
| 7,621,941 | B2 | 11/2009 | Fridolin et al. |
| 7,648,521 | B2 | 1/2010 | Hestad |
| 7,922,746 | B2 | 4/2011 | Miller |
| 8,021,399 | B2 | 9/2011 | Ritland |
| 8,167,908 | B2 | 5/2012 | Ely et al. |
| 8,246,657 | B1 | 8/2012 | Samuel |
| 8,430,916 | B1 | 4/2013 | Winslow et al. |
| 8,758,411 | B1* | 6/2014 | Rayon ................. A61B 17/7049 |
| | | | 606/259 |
| 9,101,405 | B2 | 8/2015 | Dickinson et al. |
| 9,451,994 | B1 | 9/2016 | Whipple et al. |
| 9,724,131 | B2 | 8/2017 | Bootwala et al. |
| 11,020,151 | B2 | 6/2021 | Bootwala et al. |
| 11,846,500 | B2 | 12/2023 | Morozov et al. |
| 2004/0210216 | A1 | 10/2004 | Farris et al. |
| 2005/0113831 | A1 | 5/2005 | Franck et al. |
| 2005/0228378 | A1 | 10/2005 | Kalfas et al. |
| 2006/0025770 | A1* | 2/2006 | Schlapfer ........... A61B 17/7007 |
| | | | 606/328 |
| 2006/0177263 | A1 | 8/2006 | Thomke et al. |
| 2007/0038217 | A1* | 2/2007 | Brown ............... A61B 17/6466 |
| | | | 606/57 |
| 2007/0238335 | A1 | 10/2007 | Veldman et al. |
| 2007/0270817 | A1 | 11/2007 | Rezach |
| 2008/0228184 | A1 | 9/2008 | Hestad |
| 2009/0036929 | A1 | 2/2009 | Reglos et al. |
| 2009/0105765 | A1 | 4/2009 | Strnad |
| 2009/0148232 | A1 | 6/2009 | Thomke et al. |
| 2009/0198281 | A1 | 8/2009 | Rice et al. |
| 2009/0254086 | A1 | 10/2009 | Trilla-Muntanola |
| 2010/0324599 | A1 | 12/2010 | Montello et al. |
| 2011/0087287 | A1 | 4/2011 | Reeder, Jr. et al. |
| 2011/0118786 | A1 | 5/2011 | Jang |
| 2012/0029571 | A1 | 2/2012 | Schwab et al. |
| 2013/0079826 | A1* | 3/2013 | Simonson .......... A61B 17/8685 |
| | | | 606/264 |
| 2013/0096617 | A1 | 4/2013 | Ballard et al. |
| 2013/0150887 | A1 | 6/2013 | McLean et al. |
| 2013/0268004 | A1* | 10/2013 | Rathbun ............ A61B 17/7049 |
| | | | 606/252 |
| 2013/0268804 | A1 | 10/2013 | Ronen et al. |
| 2013/0304131 | A1 | 11/2013 | McLean et al. |
| 2014/0052189 | A1 | 2/2014 | Hammer |
| 2016/0089187 | A1 | 3/2016 | Bootwala et al. |
| 2017/0281243 | A1 | 10/2017 | Murray |
| 2017/0281247 | A1 | 10/2017 | Murray et al. |
| 2017/0290611 | A1 | 10/2017 | Bootwala et al. |
| 2018/0098798 | A1 | 4/2018 | Italiaie et al. |
| 2018/0310963 | A1 | 11/2018 | Khajavi et al. |
| 2021/0259745 | A1 | 8/2021 | Bootwala et al. |

FOREIGN PATENT DOCUMENTS

| | | |
|---|---|---|
| JP | 2005516723 A | 6/2005 |
| JP | 2009532182 A | 9/2009 |
| WO | 2006025919 A2 | 3/2006 |
| WO | 2008027940 A1 | 3/2008 |
| WO | 2013085958 A1 | 6/2013 |

OTHER PUBLICATIONS

International Search Report for Application No. PCT/US2015/051172, mailed Jan. 7, 2016 (8 pages).

Japanese Office Action for Application No. 2017-516476, mailed Jul. 30, 2019 (17 pages).

Written Opinion for Application No. PCT/US2015/051172, mailed Jan. 7, 2016 (7 pages).

U.S. Appl. No. 14/496,804, filed Sep. 25, 2014, Spinal Connectors and Related Methods.

U.S. Appl. No. 15/634,022, filed Jun. 27, 2017, Spinal Connectors and Related Methods.

U.S. Appl. No. 17/319,033, filed May 12, 2021, Spinal Connectors and Related Methods.

* cited by examiner

FIG. 6A
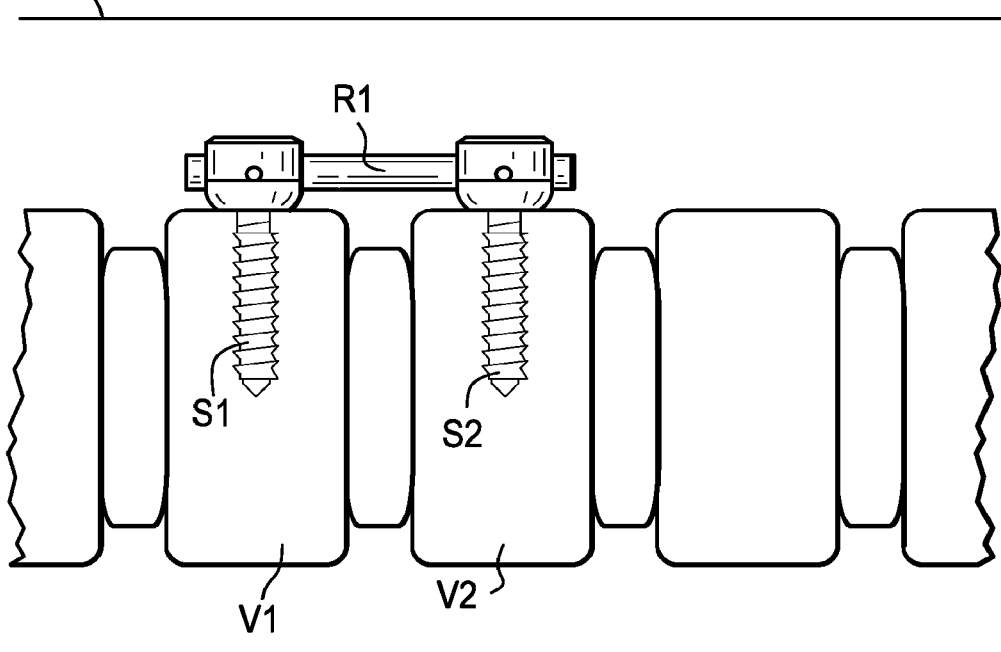
FIG. 6B
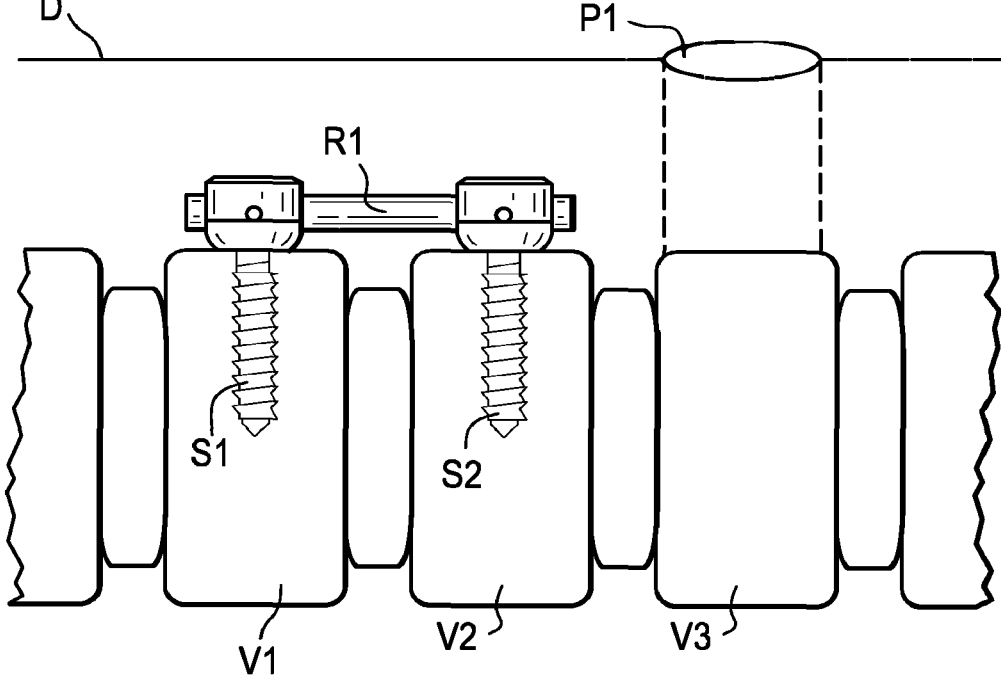

SPINAL CONNECTORS AND RELATED METHODS

CROSS-REFERENCE TO RELATED APPLICATIONS

This application is a continuation of U.S. application Ser. No. 17/319,033, filed on May 12, 2021. U.S. application Ser. No. 17/319,033 is a continuation of U.S. application Ser. No. 15/634,022, filed on Jun. 27, 2017 (issued as U.S. Pat. No. 11,020,151). U.S. application Ser. No. 15/634,022 is a continuation of U.S. application Ser. No. 14/496,804 filed on Sep. 25, 2014 (issued as U.S. Pat. No. 9,724,131). The entire contents of each of these applications are incorporated by reference herein.

FIELD

Spinal implant connectors and related methods are disclosed herein.

BACKGROUND

Fixation systems can be used in orthopedic surgery to align and/or fix a desired relationship between two or more bones or bone fragments. For example, in spinal surgery, spinal fixation systems can be used to align and/or fix a desired relationship between vertebral bodies. Such devices typically include a spinal fixation element, such as a relatively rigid fixation rod, that is coupled to the vertebrae by attaching the element to various anchoring devices, such as hooks, bolts, wires, or screws. The fixation element can have a predetermined or adjustable contour selected based on the desired correction or fixation. Once installed, the fixation element holds the vertebrae in a desired spatial relationship, either until desired healing or spinal fusion has taken place, or for some other period of time.

There are a number of instances in which it can be desirable to couple multiple spinal fixation elements to each other. For example, various aspects of the patient's anatomy, the surgical technique used, and/or the desired correction can require multiple spinal rods to be coupled to one another. By way of further example, there can be a desire in some revision surgeries to extend a previously-installed construct to additional vertebral levels by coupling a newly-installed spinal rod to a previously-installed rod. As yet another example, coupling multiple rods to one another can improve the overall strength and stability of an implanted construct.

Minimally-invasive surgical techniques have been developed to facilitate installation of spinal fixation systems via one or more percutaneous working channels, thereby reducing patient trauma and recovery time. These techniques, however, are often not well-suited for installing multiple fixation elements which are to be coupled to one another, or for coupling a new fixation element to a previously-installed construct during revision surgery. Even in open surgery, existing systems for coupling multiple fixation elements to one another can be cumbersome and difficult to use. Accordingly, a need exists for improved spinal connectors and related methods.

SUMMARY

In some embodiments, a connector can be configured to couple a first fixation element (e.g., a first rod) to a second fixation element (e.g., a second rod). One or both of the first and second fixation elements can be included with the connector, or one or both can be separately provided. In some instances, at least one of the fixation elements is previously implanted in a patient. The connector can provide one or more degrees of freedom between the first and second fixation elements. The connector can also include a locking element configured to (1) lock one or more of the fixation elements to the connector, and (2) lock one or more of the degrees of freedom between the fixation elements. The connector can be configured to snap onto or otherwise engage a fixation element in a manner that provides tactile and/or audible feedback to the surgeon. At least one of the fixation members can include a bend or jog to provide clearance for patient anatomy or for components of a fixation construct to which the connector is to be attached. The connector can be used in various surgical methods, including minimally-invasive revision procedures in which an existing spinal fixation construct is extended to one or more additional vertebral levels.

In some embodiments, a spinal connector includes a first spinal fixation element having a mating feature that defines an opening and a connection assembly coupled to the mating feature such that at least a portion of the connection assembly is received within the opening of the mating feature. The connection assembly can include a clamp that defines a recess configured to receive a second spinal fixation element and a locking element configured to selectively lock the clamp to the second spinal fixation element and to lock one or more degrees of freedom of the connection assembly.

The one or more degrees of freedom can include a first rotational degree of freedom by which the first spinal fixation element is rotatable with respect to the clamp about a longitudinal axis of the opening and a second rotational degree of freedom by which the first spinal fixation element is rotatable with respect to the clamp about a transverse axis of the opening. The clamp can include an elongate stud portion configured to extend through the opening of the mating feature of the first spinal fixation element such that the stud portion can rotate about a longitudinal axis of the opening and such that the stud portion can rotate about a transverse axis of the opening. The locking element can include a locking nut configured to threadably engage a stud portion of the clamp. The connection assembly can include a washer disposed around the stud portion of the clamp between the locking nut and the mating feature of the first spinal fixation element. The washer can include first and second recesses having teeth formed therein configured to mesh with corresponding teeth formed on first and second protrusions formed on the mating feature when the protrusions are at least partially received within the recesses. The clamp can include first and second arms coupled to one another at a hinge portion and an outer surface of the clamp can be tapered such that advancement of the locking element along a longitudinal axis of the clamp is effective to squeeze the arms of the clamp together. The hinge portion can include a living hinge. The spinal connector can include a coupling member extending outward from the mating feature and configured to couple the first spinal fixation element to an insertion device. The clamp can be configured to provide at least one of audible and tactile feedback when a second spinal fixation element is received in the recess. The first spinal fixation element can include a first elongate portion, a second elongate portion that is parallel to the first elongate portion and offset from the first elongate portion in one or more dimensions, and an intermediate portion connecting the first and second elongate portions. The intermediate portion can be shaped to bend around a bone anchor coupled to the second spinal fixation element when the clamp is attached to the second spinal fixation element. The mating feature can include a ring-shaped body formed integrally with the first spinal fixation element. The opening can include reliefs formed in an inner surface thereof to facilitate angulation of the clamp within the opening. The mating feature can extend longitudinally from an end portion of the first spinal fixation element. The mating feature can extend laterally from an end portion of the first spinal fixation element. The connection assembly can include a housing having first and second shoes slidably disposed therein, the locking element being configured to push the first shoe into engagement with the mating feature to lock an orientation of the first spinal fixation element relative to the housing and to push the second shoe into engagement with the second spinal fixation element to lock the second spinal fixation element in the clamp. The clamp can include an upper clamping arm and a lower clamping arm with a biasing element disposed therebetween, the locking element extending through openings formed in the upper clamping arm, the biasing element, and the lower clamping arm. The one or more degrees of freedom can include a rotational degree of freedom by which the first spinal fixation element is rotatable with respect to the upper and lower clamping arms about a longitudinal axis of the locking element.

In some embodiments, a spinal connector includes a clamp having first and second arms configured to grasp a spinal fixation element, at least a portion of the first and second arms defining a stud portion; a spinal fixation element having a mating feature that defines an opening through which the stud portion of the clamp extends; and a locking element configured to engage the stud portion to selectively move the first and second arms toward one another and to lock rotation of the stud portion about a longitudinal axis of the opening and about a transverse axis of the opening.

The locking element can include a locking nut configured to threadably engage the stud portion of the clamp. The spinal connector can include a washer disposed around the stud portion of the clamp between the locking nut and the mating feature of the spinal fixation element. The washer can include first and second recesses having surface features formed therein configured to mesh with corresponding surface features formed on first and second protrusions formed on the mating feature when the protrusions are at least partially received within the recesses. The first and second arms can be coupled to one another at a hinge portion and an outer surface of the clamp can be tapered such that advancement of the locking element along a longitudinal axis of the clamp is effective to squeeze the arms of the clamp together.

In some embodiments, a spinal connector includes a first elongate rod having a first section that is parallel to and offset from a second section, the first and second sections being joined by a transition section; a ring-shaped mating feature extending from the first section of the rod; a clamp having first and second clamping arms that define a recess therebetween in which a second elongate rod can be received, the clamp having a stud portion that extends through a central opening of the ring-shaped mating feature such that the mating feature bears against a shoulder of the stud portion and such that the stud portion is rotatable about a longitudinal axis of the central opening and about a transverse axis of the central opening; a washer disposed over the stud portion; and a locking nut threadably-engaged with the stud portion such that the washer is disposed between the locking nut and the mating feature and such that the mating feature is disposed between the washer and the shoulder. Tightening the locking nut can be effective to lock rotation of the stud portion about the longitudinal and transverse axes of the central opening and to squeeze the first and second clamping arms together to lock the clamp to a second elongate rod disposed in the recess.

One of the washer and the mating feature can include a curved recess in which a plurality of teeth are formed, the plurality of teeth being configured to engage a plurality of teeth formed on a curved protrusion formed on the other of the washer and the mating feature when the protrusion is at least partially received within the recess.

In some embodiments, a spinal connector includes a first clamping member that defines a recess configured to receive a first spinal fixation element; a second clamping member that defines a recess configured to receive a second spinal fixation element; and a locking element that extends through openings formed in the first and second clamping members, the locking element being configured to selectively lock the first clamping member to the first spinal fixation rod, lock the second clamping member to the second spinal fixation rod, and lock one or more degrees of freedom between the first and second clamping members.

The one or more degrees of freedom can include a rotational degree of freedom by which the first clamping member is rotatable with respect to the second clamping member about a longitudinal axis of the locking element and a translational degree of freedom by which the first clamping member is translatable with respect to the second clamping member along an axis that extends perpendicular to the longitudinal axis of the locking element. The second clamping member can be rotatable relative to the first clamping member about a longitudinal axis of the locking element when the locking element is in an unlocked configuration. The second clamping member can be translatable relative to the first clamping member along an axis that extends perpendicular to the longitudinal axis of the locking element when the locking element is in an unlocked configuration.

In some embodiments, a spinal fixation method includes forming a first minimally-invasive pathway to access a first vertebra; delivering a screw through the first minimally-invasive pathway; implanting the screw in the first vertebra; forming a second minimally-invasive pathway to access a first spinal fixation element coupled to at least one other vertebra; delivering a second spinal fixation element and a spinal connector coupled thereto through the second minimally-invasive pathway; moving the spinal connector relative to the second spinal fixation element about one or more degrees of freedom to position at least a portion of the second spinal fixation element in engagement with the screw; and actuating a locking element of the spinal connector to lock the spinal connector to the first spinal fixation element and to lock the one or more degrees of freedom.

Moving the spinal connector can include moving the second spinal fixation element subcutaneously into engagement with the screw. The first spinal fixation element can be a previously-implanted spinal fixation element. The spinal connector can include a clamp having a stud portion that extends through an opening of a mating feature of the second spinal fixation element, and the one or more degrees of freedom can include a first rotational degree of freedom by which the second spinal fixation element is rotatable with respect to the clamp about a longitudinal axis of the opening and a second rotational degree of freedom by which the second spinal fixation element is rotatable with respect to the clamp about a transverse axis of the opening. The spinal connector can include a clamp having a stud portion that extends through an opening of a mating feature of the second spinal fixation element, and moving the spinal connector can include pivoting the stud portion about a longitudinal axis of the central opening and about a transverse axis of the central opening. The spinal connector can include a clamp having a stud portion that extends through an opening of a mating feature of the second spinal fixation element, and actuating the locking element can include tightening a locking nut that is threadably engaged with the stud portion to compress the mating feature against a shoulder of the stud portion. The spinal connector can include a clamp having a stud portion that extends through an opening of a mating feature of the second spinal fixation element and a washer disposed around the stud portion, and moving the spinal connector can include engaging surface features formed on the washer with corresponding surface features formed on the mating feature. The spinal connector can include first and second arms coupled to one another at a hinge portion and having tapered outer surfaces, and actuating the locking element can include advancing a locking nut along the first and second arms to squeeze the arms together. Actuating the locking element can consist only of rotating a single locking element. The method can include positioning the second spinal fixation element such that the second spinal fixation element extends around a bone anchor secured to the first spinal fixation element. The method can include attaching the spinal connector to the first spinal fixation element at a location intermediate first and second bone anchors securing the first spinal fixation element to bone.

In some embodiments, a spinal fixation method includes forming a first minimally-invasive pathway to access a first vertebra; delivering a screw through the first minimally-invasive pathway; implanting the screw in the first vertebra; forming a second minimally-invasive pathway to access a first spinal fixation element coupled to at least one other vertebra; delivering a second spinal fixation element through the first minimally-invasive pathway to position a portion of the second spinal fixation element in the second minimally-invasive pathway; inserting a spinal connector through the second minimally-invasive pathway and coupling the spinal connector to the first and second spinal fixation elements; and securing the second spinal fixation element to the screw.

Coupling the spinal connector can include adjusting one or more degrees of freedom of the spinal connector to position the spinal connector with respect to the first and second spinal fixation elements; and actuating a locking element of the spinal connector to lock the spinal connector to the first and second spinal fixation elements and to lock the one or more degrees of freedom.

In some embodiments, a spinal fixation method includes clamping a spinal connector having a first spinal fixation element coupled thereto onto a second spinal fixation element; and actuating a locking mechanism of the spinal connector to simultaneously lock the spinal connector to the second spinal fixation element and to lock one or more degrees of freedom between the spinal connector and the first spinal fixation element.

The present invention further provides devices and methods as claimed.

BRIEF DESCRIPTION OF THE DRAWINGS

The invention will be more fully understood from the following detailed description taken in conjunction with the accompanying drawings, in which:

FIGS. 6A-6G schematically illustrate a spinal fixation method.

DETAILED DESCRIPTION

Figure 1A:
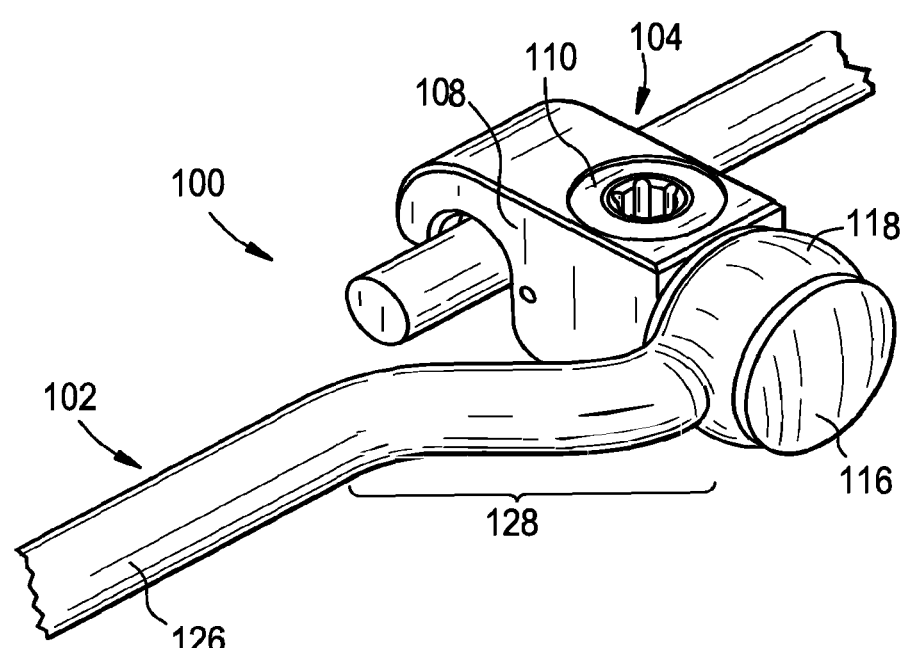
FIG. 1A is a perspective view of a spinal connector coupled to a spinal fixation element.
Figure 1B:
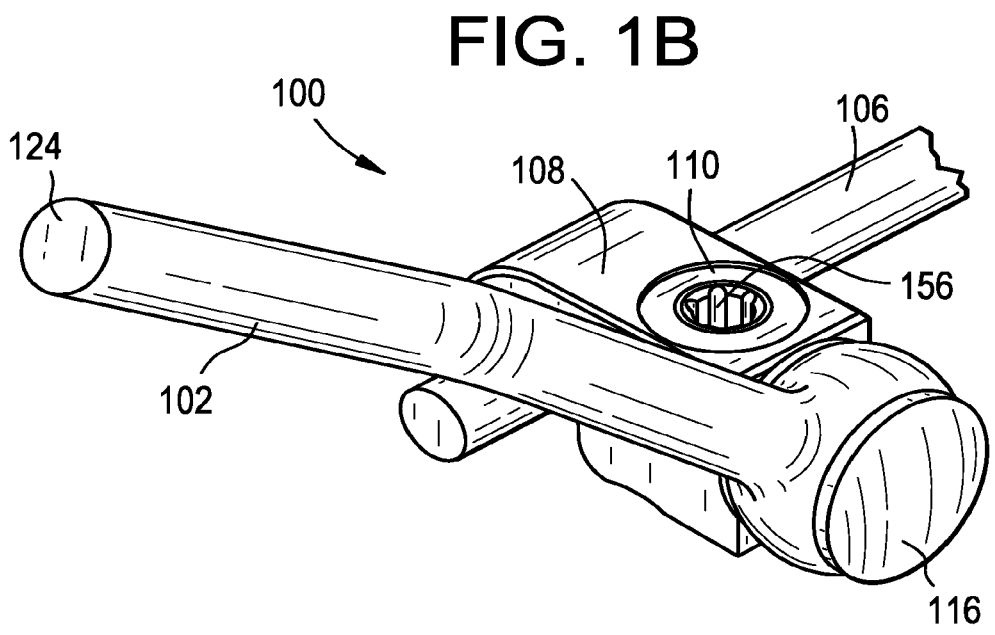
FIG. 1B is another perspective view of the spinal connector and the spinal fixation element of FIG. 1A.
Figure 1C:
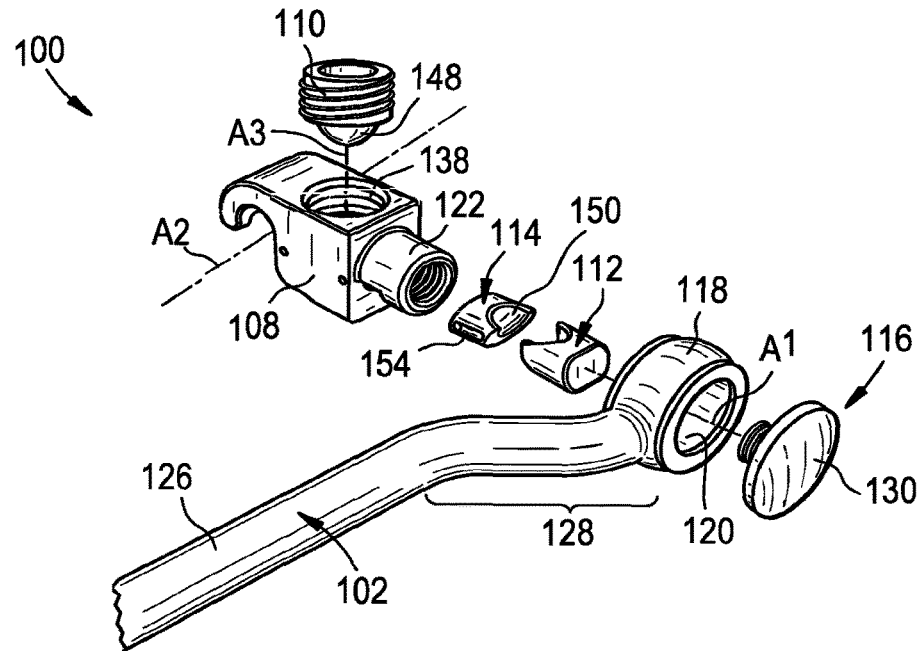
FIG. 1C is an exploded perspective view of the spinal connector of FIG. 1A.

In some embodiments, a connector can be configured to couple a first fixation element (e.g., a first rod) to a second fixation element (e.g., a second rod). One or both of the first and second fixation elements can be included with the connector, or one or both can be separately provided. In some instances, at least one of the fixation elements is previously implanted in a patient. The connector can provide one or more degrees of freedom between the first and second fixation elements. The connector can also include a locking element configured to (1) lock one or more of the fixation elements to the connector, and (2) lock one or more of the degrees of freedom between the fixation elements. The connector can be configured to snap onto or otherwise engage a fixation element in a manner that provides tactile and/or audible feedback to the surgeon. At least one of the fixation members can include a bend or jog to provide clearance for patient anatomy or for components of a fixation construct to which the connector is to be attached. The connector can be used in various surgical methods, including minimally-invasive revision procedures in which an existing spinal fixation construct is extended to one or more additional vertebral levels.

Certain exemplary embodiments will now be described to provide an overall understanding of the principles of the structure, function, manufacture, and use of the devices and methods disclosed herein. One or more examples of these embodiments are illustrated in the accompanying drawings. Those of skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

FIGS. 1A-1E illustrate an exemplary embodiment of a spinal connector 100. The connector 100 generally includes a first spinal fixation element 102 and a connection assembly 104 for coupling the first spinal fixation element 102 to a second spinal fixation element 106. The second spinal fixation element 106 can be a previously-implanted spinal fixation element to which the connector 100 is to be coupled or can be implanted with the connector 100 or as part of the same procedure as the connector 100. The connection assembly 104 can include a locking mechanism for selectively locking an orientation of the first spinal fixation element 102 relative to the connection assembly 104 and for locking a position and an orientation of the connection assembly relative to the second spinal fixation element 106. As shown, the connection assembly 104 can include a housing 108, a set screw 110, first and second shoes 112, 114, and a retaining cap 116.

In the illustrated embodiment, the first and second spinal fixation elements 102, 106 are elongate spinal rods, though it will be appreciated that any of a variety of fixation elements can be used instead or in addition, such as bone plates. The first spinal fixation element 102 can include a mating feature 118 formed on or coupled to a first terminal end thereof configured to rotatably couple the first spinal fixation element to the housing 108. In the illustrated embodiment, the mating feature 118 is a ring-shaped structure formed integrally with the first spinal fixation element 102. The mating feature 118 can include a central opening 120 configured to receive a post 122 that extends laterally-outward from the housing 108 such that the mating feature is rotatable about the post (e.g., about a longitudinal axis of the post). Stated differently, the housing 108 can be rotatable about a longitudinal axis A1 of the central opening 120. A second, opposite terminal end 124 of the first spinal fixation element 102 can be configured to facilitate minimally-invasive insertion of the first spinal fixation element. For example, the second terminal end 124 can be rounded, bulleted, tapered, etc. to allow for atraumatic tunneling of the first spinal fixation element 102 subcutaneously from an insertion portal to a final implanted position.

The first spinal fixation element 102 can be completely straight or can include one or more bends, curves, joints, offsets, jogs, etc. For example, the first spinal fixation element 102 can have an S-shaped or Z-shaped bend to provide clearance for patient anatomy or for a portion (e.g., a bone screw) of a fixation construct to which the connector 100 is to be coupled. In the illustrated embodiment, the first spinal fixation element 102 includes a straight portion 126 joined by a curved portion 128 to the mating feature 118. The curved portion 128 can provide an offset such that the first spinal fixation element 102 can bend around a portion of the patient's anatomy or a portion of a fixation construct to which the connector 100 is coupled. Accordingly, a low-profile construct can be formed, with the straight portion 126 of the first spinal fixation element 102 positioned as a natural extension of the second spinal fixation element 106. It will thus be appreciated that the connector 100 can be clamped onto a previously-installed second spinal fixation element 106, intermediate to first and second bone anchors securing the second spinal fixation element, without the first spinal fixation element 102 interfering with the bone anchors. The first spinal fixation element 102 can be rigid, can be bendable or malleable, or can include both rigid portions and bendable portions. Thus, in some embodiments, the contour of the first spinal fixation element 102 can be adjusted as needed for a particular procedure, either manually or with the assistance of bending tools.

The retaining cap 116 can be configured to retain the mating feature 118 of the first spinal fixation element 102 on the post 122 of the housing 108, while still allowing the first spinal fixation element to rotate about the post. The retaining cap 116 can include a disc-shaped cover 130 with a pin 132 extending therefrom. The pin 132 can be received within the post 122 of the housing 108 to capture the mating feature 118 between the housing and the cover 130. The exterior of the pin 132 and the interior of the post 122 can include corresponding threads to threadably engage one another. While a threaded engagement is shown, it will be appreciated that any of a variety of other techniques can be used to couple the retaining cap 116 to the housing 108. For example, the pin 132 can be press-fit, welded, cross-pinned, and/or glued to the post 122.

The housing 108 can include a clamp portion 134 in which the second spinal fixation element 106 can be received. The clamp portion 134 can be formed on a side of the housing 108 opposite to the side of the housing from which the post 122 extends. Alternatively, the clamp portion 134 can be formed on a side of the housing adjacent to the side from which the post 122 extends.

The clamp portion 134 can include a recess 136 sized and/or shaped according to the second spinal fixation element 106 to which the connector 100 is to be coupled. For example, a diameter of the recess 136 can be substantially equal to a diameter of the second spinal fixation element 106. Alternatively, the diameter of the recess 136 can be slightly less than the diameter of the second spinal fixation element 106 to allow for a snap-fit engagement that provides tactile and/or audible feedback to the surgeon when the connector 100 "snaps" onto the second spinal fixation element. As discussed further below, this feedback can be advantageous, particularly in minimally-invasive revision surgery. As another alternative, the diameter of the recess 136 can be slightly greater than that of the second spinal fixation element 106, with any play being taken up by the second shoe 114 when the locking mechanism of the connector 100 is actuated, as described below. The spinal connector 100 can thus be configured to couple to second spinal fixation elements of various sizes or shapes. In some embodiments, a plurality of spinal connectors 100, each having recesses 136 with different sizes or shapes, can be provided as part of a kit to allow for selection of a connector sized and shaped appropriately for a particular application.

While the illustrated recess 136 forms a portion of a cylinder, it will be appreciated that the recess can have various other shapes depending on the shape of the second spinal fixation element 106 to which the connector 100 is to be coupled. For example, in the case of a second spinal fixation element 106 with a rectangular cross-section, the recess 136 can have a corresponding rectangular shape.

The recess 136 can have a longitudinal axis A2 that extends perpendicular to the longitudinal axis A1 of the central opening 120. Thus, the longitudinal axis A2 of the recess 136 can be perpendicular to a rotation axis about which the first spinal fixation element 102 rotates relative to the housing 108. In such embodiments, when a second spinal fixation element 106 is received in the recess 136, the first spinal fixation element 102 can be rotatable about an axis perpendicular to a longitudinal axis of the second spinal fixation element 106. The clamp portion 134 of the housing 108 that defines the recess 136 can be configured to extend around any portion of the second spinal fixation element 106. In the illustrated embodiment, the clamp portion 134 is sized to extend around approximately 200 degrees of the circumference of the second spinal fixation element 106. In other embodiments, the clamp portion 134 can cover a greater or lesser extent of the circumference of the second spinal fixation element 106. For example, the extent of coverage can be between about 160 degrees and about 240 degrees of the circumference of the second spinal fixation element 106.

Figure 1D:
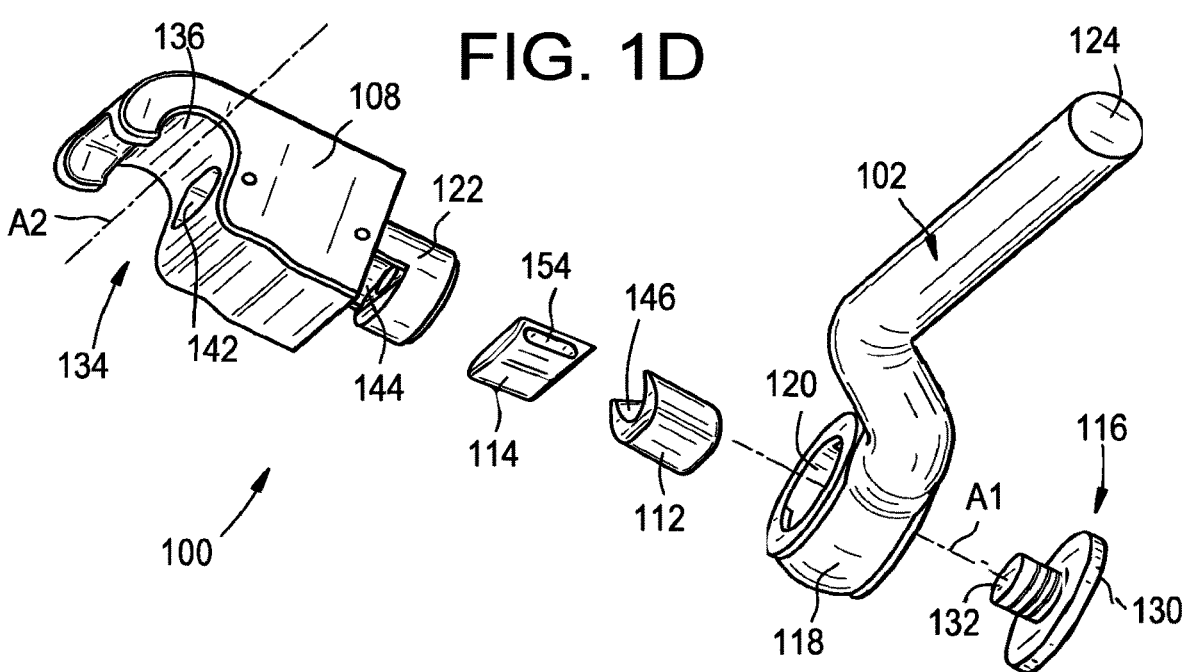
FIG. 1D is another exploded perspective view of the spinal connector of FIG. 1A.
Figure 1E:
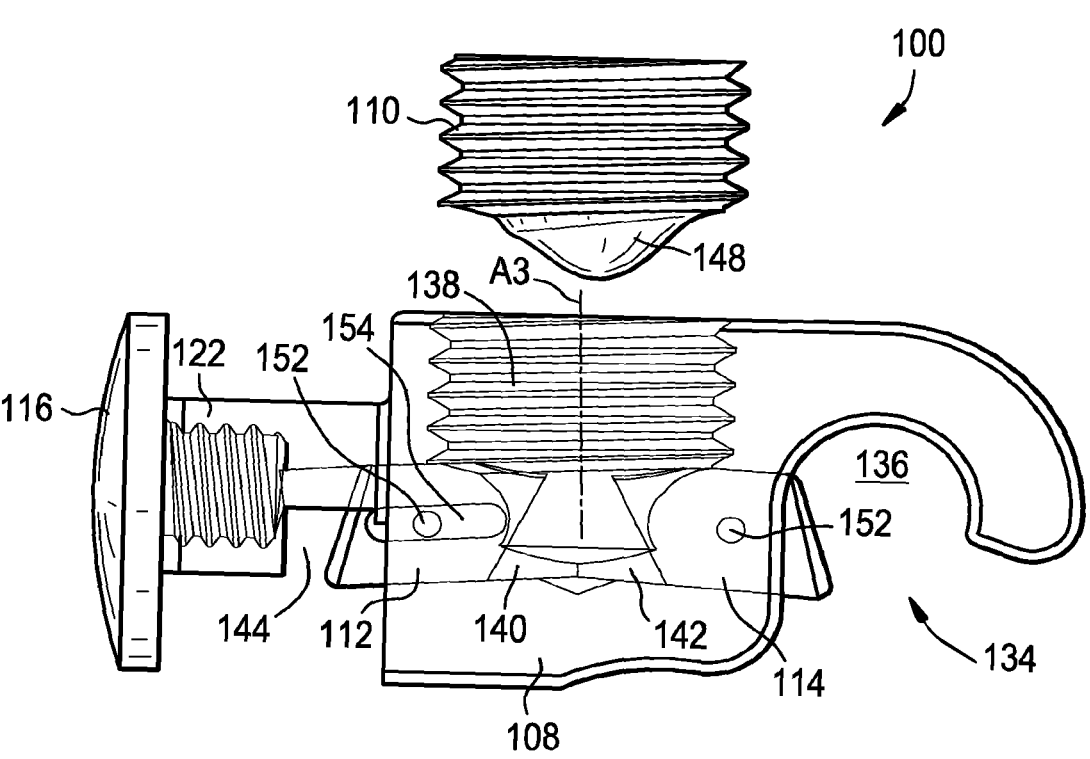
FIG. 1E is a sectional, partially-exploded, profile view of the spinal connector of FIG. 1A with a spinal fixation element component of the connector omitted.

The housing 108 can include an opening in which a locking element is received. For example, as shown, the housing 108 can include an internally-threaded bore hole 138 configured to receive an externally-threaded set screw 110. As best seen in FIG. 1E, the housing 108 can also include first and second channels 140, 142 in which the first and second shoes 112, 114 are slidably received, respectively. The first channel 140 can extend from the threaded bore hole 138 to a sidewall opening 144 formed in the post 122. As best shown in FIG. 1D, the second channel 142 can be open to the recess 136 and can extend from the recess to the threaded bore hole 138.

The first shoe 112 can be slidable within the first channel 140 between an extended position in which the first shoe protrudes through the post 122 and a retracted position in which the first shoe does not protrude through the post or protrudes though the post to a lesser extent. In the extended position, the first shoe 112 can engage the interior sidewall of the mating feature 118 to resist or prevent rotation of the first spinal fixation element 102 about the post 122. In the retracted position, the first shoe 112 does not engage, or only lightly-engages, the mating feature 118 such that the first spinal fixation element 102 is freely-rotatable about the post 122. The surface of the first shoe 112 configured to engage the mating feature 118 can include teeth, serrations, or other gripping features or surface treatments to provide enhanced purchase with the mating feature. An opposite surface of the first shoe 112 configured to be engaged by the locking element can be shaped to match the shape of the locking element and to encourage sliding movement of the first shoe as the locking element is advanced within the opening 138. For example, the first shoe 112 can define a ramped or concave surface 146 sized to match a convex distal tip 148 of the locking element 110.

The second shoe 114 can be slidable within the second channel 142 between an extended position in which the second shoe protrudes into the recess 136 and a retracted position in which the second shoe does not protrude into the recess or protrudes into the recess to a lesser extent. In the extended position, the second shoe 114 can engage a second spinal fixation element 106 disposed within the recess 136 to clamp the connector 100 to the second spinal fixation element, resisting or preventing relative movement between the two (e.g., rotation and/or longitudinal translation). In the retracted position, the second shoe 114 does not interfere with positioning of a second spinal fixation element 106 within the recess 136 and allows the connector 100 to be slid along the second spinal fixation element 106 to a desired location and rotated about the second spinal fixation element 106 to a desired orientation. The surface of the second shoe 114 configured to engage the second spinal fixation element 106 can be shaped in accordance with a type of the second spinal fixation element. For example, when the connector 100 is to be coupled to a cylindrical fixation rod, the surface can have a radius of curvature that matches the radius of the rod, or that substantially matches (i.e., is slightly less than or greater than) the radius of the rod. The surface can include teeth, serrations, or other gripping features or surface treatments to provide enhanced purchase with the second spinal fixation element 106. An opposite surface of the second shoe 114 configured to be engaged by the locking element can be shaped to match the shape of the locking element and to encourage sliding movement of the second shoe as the locking element is advanced within the opening 138. For example, the second shoe 114 can define a ramped or concave surface 150 sized to match a convex distal tip 148 of the locking element 110.

The housing 108 can include one or more retention pins 152 configured to limit the travel of the first and/or second shoes 112, 114 (e.g., to prevent the shoes from inadvertently falling out of the connector 100). In the illustrated embodiment, the pins 152 extend into the first and second channels 140, 142 of the housing 108 and are slidably received within slots or grooves 154 formed in the first and second shoes 112, 114.

As the locking element 110 is advanced within the opening, it can engage the first shoe 112 and cause the first shoe to slide within the first channel 140 into engagement with the interior sidewall of the mating feature 118 of the first spinal fixation element 102. Simultaneously, the locking element 110 can engage the second shoe 114 and cause the second shoe to slide within the second channel 142 into engagement with a second spinal fixation element 106 disposed within the recess 136. In the illustrated embodiment, the first and second channels 140, 142 extend downward and laterally-outward from the opening 138 such that the first and second shoes 112, 114 translate along linear paths between the retracted and extended positions. In other embodiments, one or both of the first and second channels 140, 142 can extend only downwardly or only outwardly. In still further embodiments, the first and second shoes 112, 114 can be configured to rotate between the extended and retracted positions without linear translational movement or in combination with linear translational movement. For example, the first and second shoes 112, 114 can be mounted on respective pivot pins such that they are rotatable relative to the housing 108 between the extended and retracted positions.

While any of a variety of locking elements can be used, in the illustrated embodiment, the locking element comprises an externally threaded set screw 110. The set screw 110 can threadably engage corresponding interior threads of the opening 138 such that rotation of the set screw in a first direction is effective to advance the set screw into the housing 108 and rotation of the set screw in a second, opposite direction is effective to withdraw the set screw relative to the housing. A longitudinal axis A3 of the opening can extend perpendicular to the longitudinal axis A2 of the recess and perpendicular to the rotation axis of the first spinal fixation element 102 about the post 122 (e.g., to the longitudinal axis A1 of the central opening 120). The length of the set screw 110 can be substantially equal to the depth of the opening 138 such that, when fully-seated in the opening, the top surface of the set screw sits flush with the top surface of the housing 108. The set screw 110 can include a driving interface 156 configured to receive or engage a screwdriver, wrench, or other instrument for rotating the set screw. The distal tip 148 of the set screw 110 can include an engagement surface for engaging the first and second shoes 112, 114. For example, the distal tip 148 of the set screw 110 can be conical, tapered, bulleted, convex, etc. to provide a camming surface that bears against the first and second shoes 112, 114 to urge the shoes towards their respective extended positions. While a single set screw 110 is shown, it will be appreciated that the connector 100 can include a plurality of set screws (e.g., a first set screw configured to engage the first shoe 112 and selectively lock rotation of the first spinal fixation element 102 relative to the housing 108 and a second set screw configured to engage the second shoe 114 and selectively clamp the housing 108 to the second spinal fixation element 106).

In use, the spinal connector 100 can be positioned in a surgical site (e.g., using a minimally-invasive technique as described in detail below). A previously-placed second spinal fixation element 106 can be positioned within the recess 136 and the housing 108 can be moved to a desired position and/or orientation with respect to the second spinal fixation element 106. In addition, the first spinal fixation element 102 can be rotated to a desired position. As the set screw 110 is tightened, the first and second shoes 112, 114 can be urged within the first and second channels 140, 142 into engagement with the mating feature 118 and the second spinal fixation element 106, respectively. The first shoe 112 can engage the mating feature 118 to lock the rotational position of the first spinal fixation element 102 relative to the housing 108. At the same time or at substantially the same time, the second shoe 114 can engage the second spinal fixation element 106 to clamp the housing 108 thereto and lock the position and orientation of the housing 108 relative to the second spinal fixation element 106. Actuation of a single locking mechanism can thus be effective to both (1) lock an orientation of a first spinal fixation element rotatably coupled to the connector and (2) lock a position and an orientation of the connector relative to a second spinal fixation element. This multiple functionality of locking onto a second spinal fixation element and locking one or more degrees of freedom of the connector can be particularly advantageous in minimally-invasive surgery, as access is only required to a single locking mechanism and two or more functions can be performed in a single step.

The spinal connector 100 can be coupled to the second spinal fixation element 106 in any of a variety of orientations. For example, the spinal connector 100 can be coupled to the second spinal fixation element 106 such that the driving interface 156 of the set screw 110 faces in a posterior direction relative to the patient and such that the set screw is advanced along an anterior-posterior axis to lock the connector. By way of further example, the spinal connector 100 can be coupled to the second spinal fixation element 106 such that the driving interface 156 of the set screw 110 faces in a medial or lateral direction relative to the patient and the set screw is advanced along a medial-lateral axis to lock the connector. The spinal connector 100 can also be coupled to the second spinal fixation element 106 in any orientation between the above two examples and at any point along a length of the second spinal fixation element.

FIGS. 2A-2H illustrate another exemplary embodiment of a spinal connector 200. The connector can include first and second clamping members 202, 204 configured to grasp first and second spinal fixation elements 206, 208, respectively. The connector 200 can also include a locking mechanism (e.g., a locking bolt 210 and locking nut 212 as shown) configured to selectively lock the first and second clamping members 202, 204 to the first and second spinal fixation elements 206, 208 and to lock one or more degrees of freedom of the connector 200.

The first clamping member 202 can include opposed arms 214 coupled to one another at a hinge portion 216. While a living hinge 216 is shown, it will be appreciated that any of a variety of hinge mechanisms can be used. For example, the opposed arms 214 can be rotatably coupled to one another about a pivot pin. The opposed arms 214 can each include a mating portion 218 in which a recess 220 is formed for receiving a first spinal fixation element 206. Each of the opposed arms 214 can also include a main portion 222 disposed between the hinge portion 216 and the mating portion 218. The opposed arms 214 can be positionable in an unlocked position in which a slot 224 defined between the main portions 222 of the arms has substantially parallel sidewalls and in which the first clamping member 202 is movable with respect to a first spinal fixation element 206 disposed between the mating portions 218 of the arms. The opposed arms 214 can also be positionable in a locked position in which the main portions 222 of the arms are deflected towards one another about the hinge portion 216 and in which a first spinal fixation element 206 disposed between the mating portions 218 of the arms is locked to the first clamping member 202 to resist or prevent rotation or sliding movement of the first spinal fixation element relative to the first clamping member.

The mating portions 218 can define a recess 220 therebetween sized and/or shaped according to the first spinal fixation element 206 to which the first clamping member 202 is to be coupled. For example, a diameter of the recess 220 can be substantially equal to a diameter of the first spinal fixation element 206. Alternatively, the diameter of the recess 220 can be slightly less than the diameter of the first spinal fixation element 206 to allow for a snap-fit engagement that provides tactile and/or audible feedback to the surgeon when the first clamping member 202 "snaps" onto the spinal fixation element 206. As discussed further below, this feedback can be advantageous, particularly in minimally-invasive revision surgery. As another alternative, the diameter of the recess 220 can be slightly greater than that of the first spinal fixation element 206 to which the connector 200 is to be coupled, with any play being taken up by the clamping action when the locking bolt 210 and locking nut 212 are tightened. The first clamping member 202 can thus be configured to couple to first spinal fixation elements of various sizes or shapes. In some embodiments, a plurality of clamping members 202, each having recesses 220 with different sizes or shapes, can be provided as part of a kit to allow for selection of a clamping member sized and shaped appropriately for a particular application.

Figure 2A:
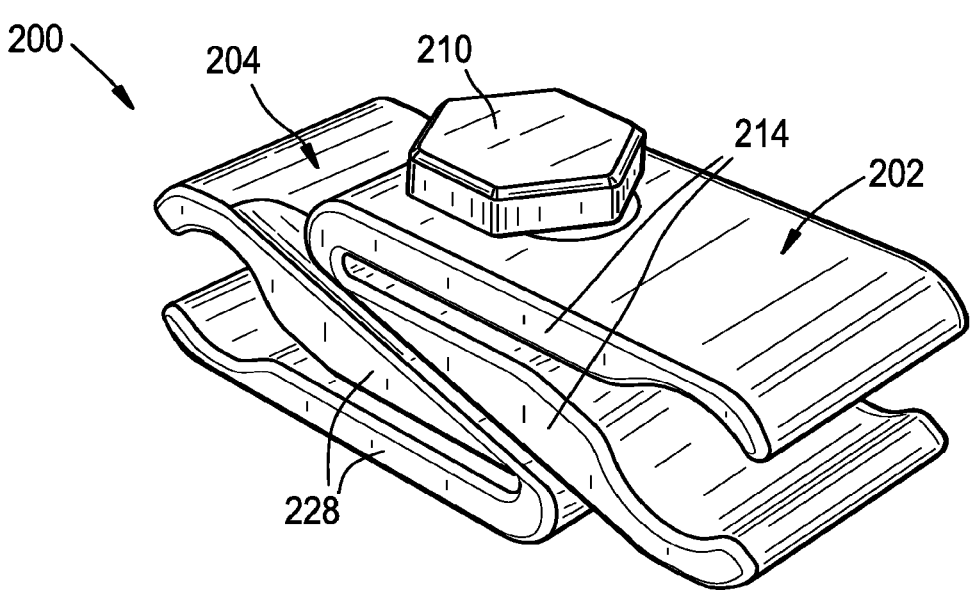
FIG. 2A is a perspective view of another spinal connector.
Figure 2B:
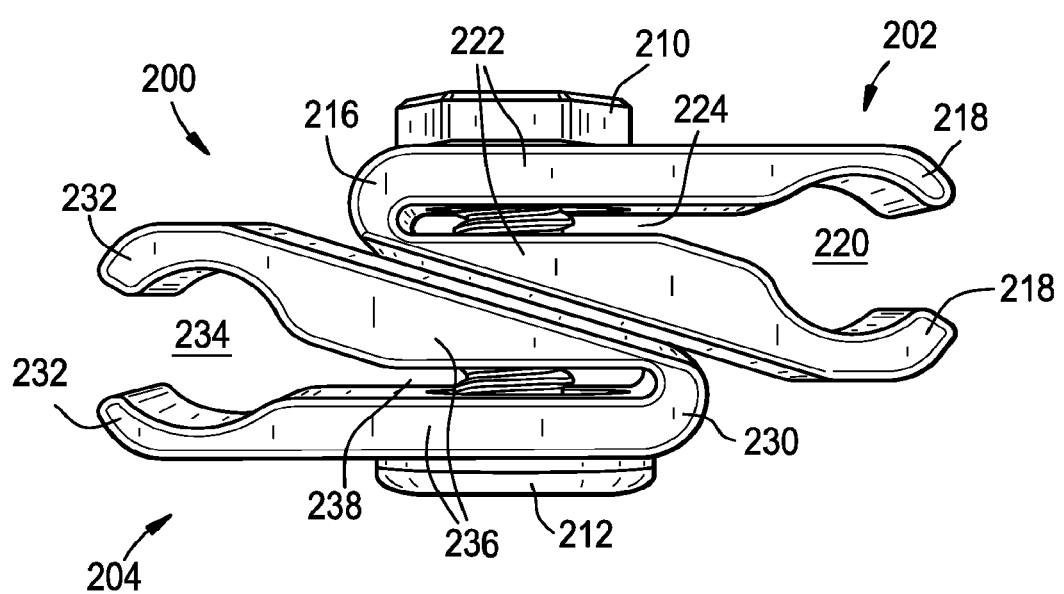
FIG. 2B is a profile view of the spinal connector of FIG. 2A.
Figure 2C:
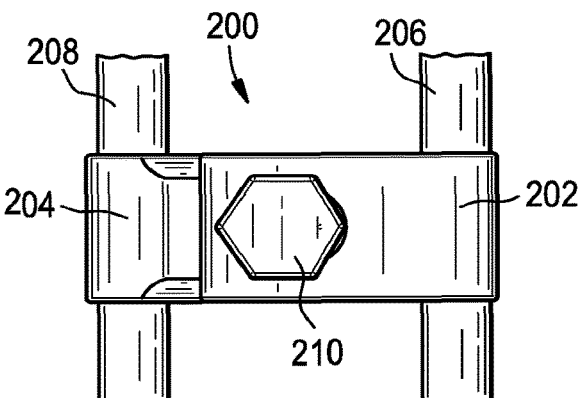
FIG. 2C is a plan view of the spinal connector of FIG. 2A coupled to first and second spinal fixation elements.
Figure 2D:
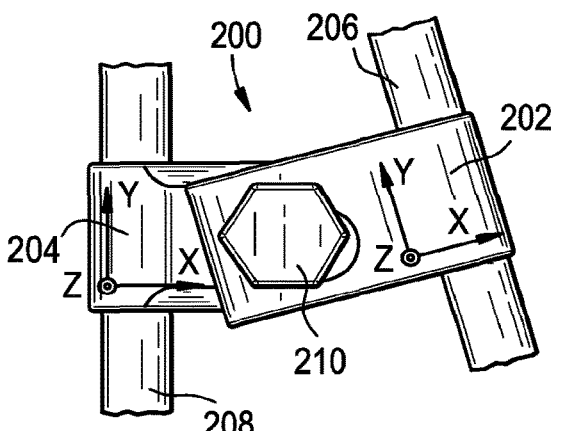
FIG. 2D is another plan view of the spinal connector of FIG. 2A coupled to first and second spinal fixation elements.
Figure 2E:
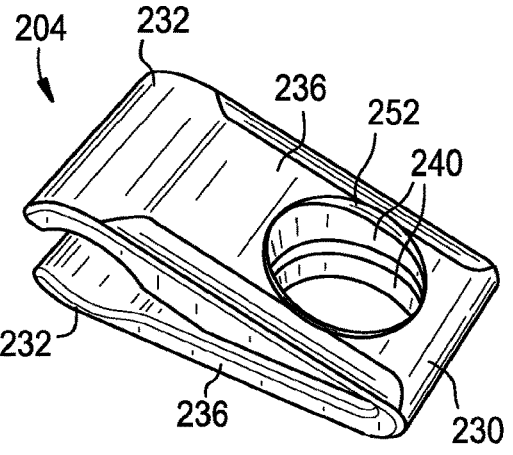
FIG. 2E is a perspective view of a second clamping member of the spinal connector of FIG. 2A.
Figure 2F:
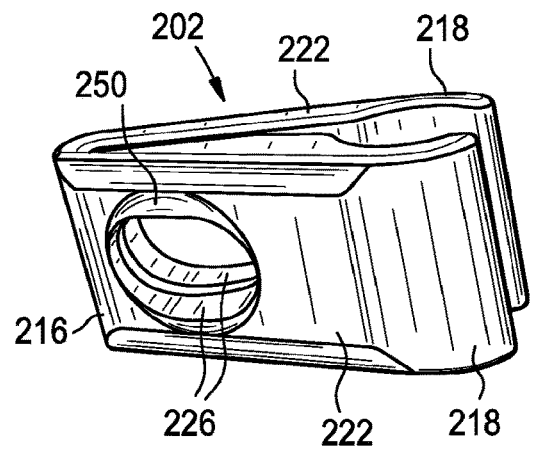
FIG. 2F is a perspective view of a first clamping member of the spinal connector of FIG. 2A.
Figures 2G, 2H:
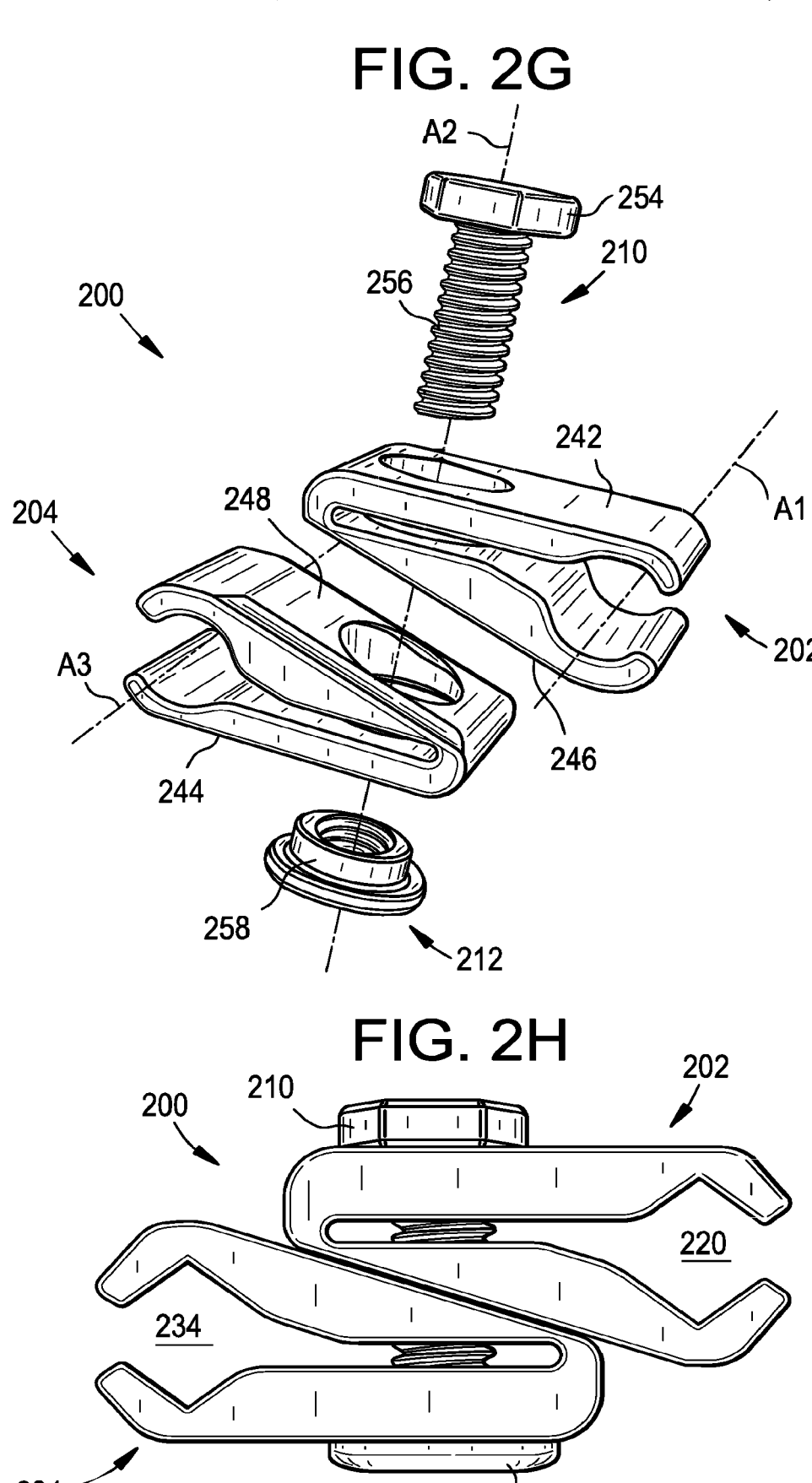
FIG. 2G is an exploded perspective view of the spinal connector of FIG. 2A.
FIG. 2H is a profile view of the spinal connector of FIG. 2A with an alternate recess shape.
Figures 3A, 3B:
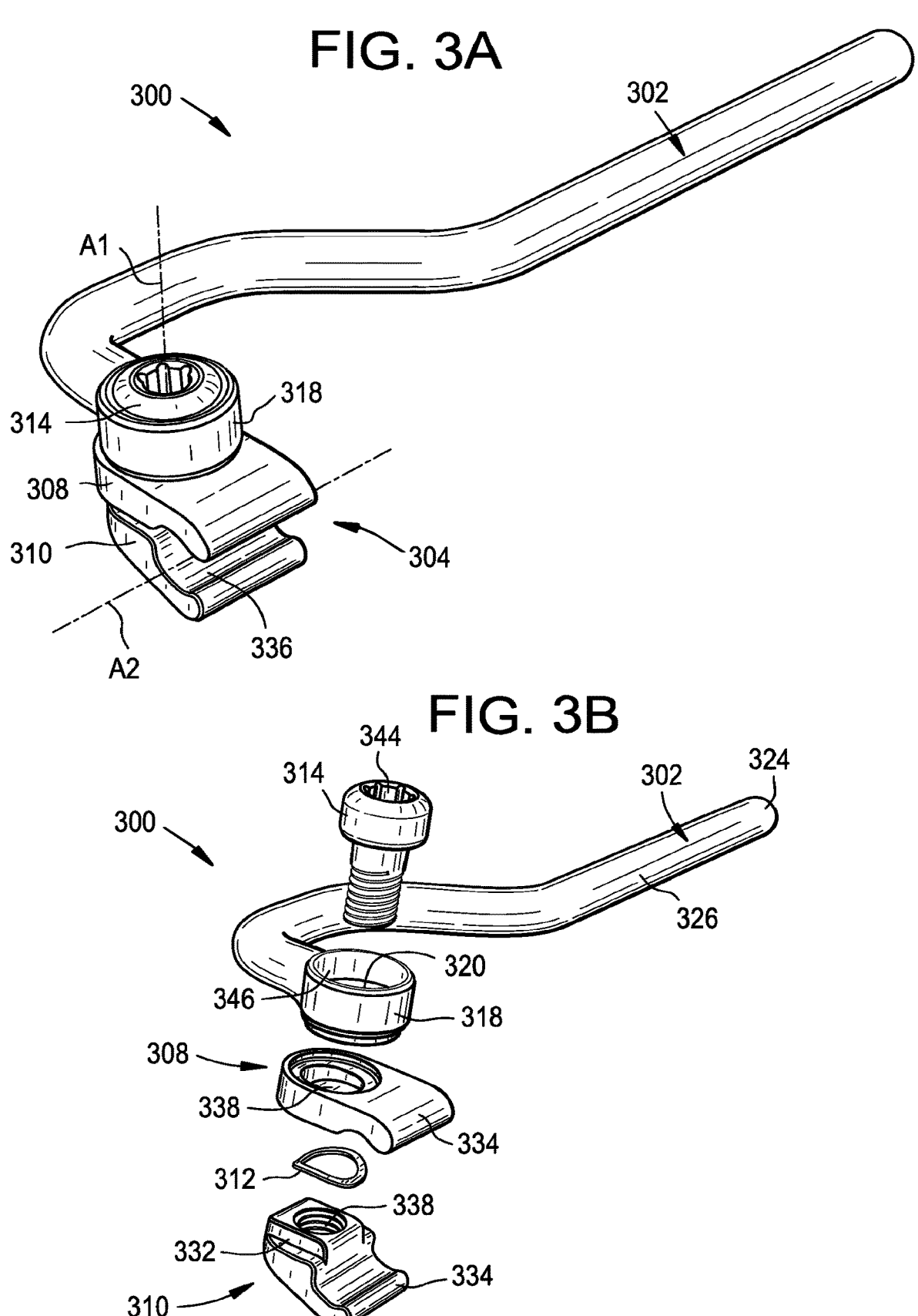
FIG. 3A is a perspective view of another spinal connector.
FIG. 3B is an exploded perspective view of the spinal connector of FIG. 3A.
Figure 3C:
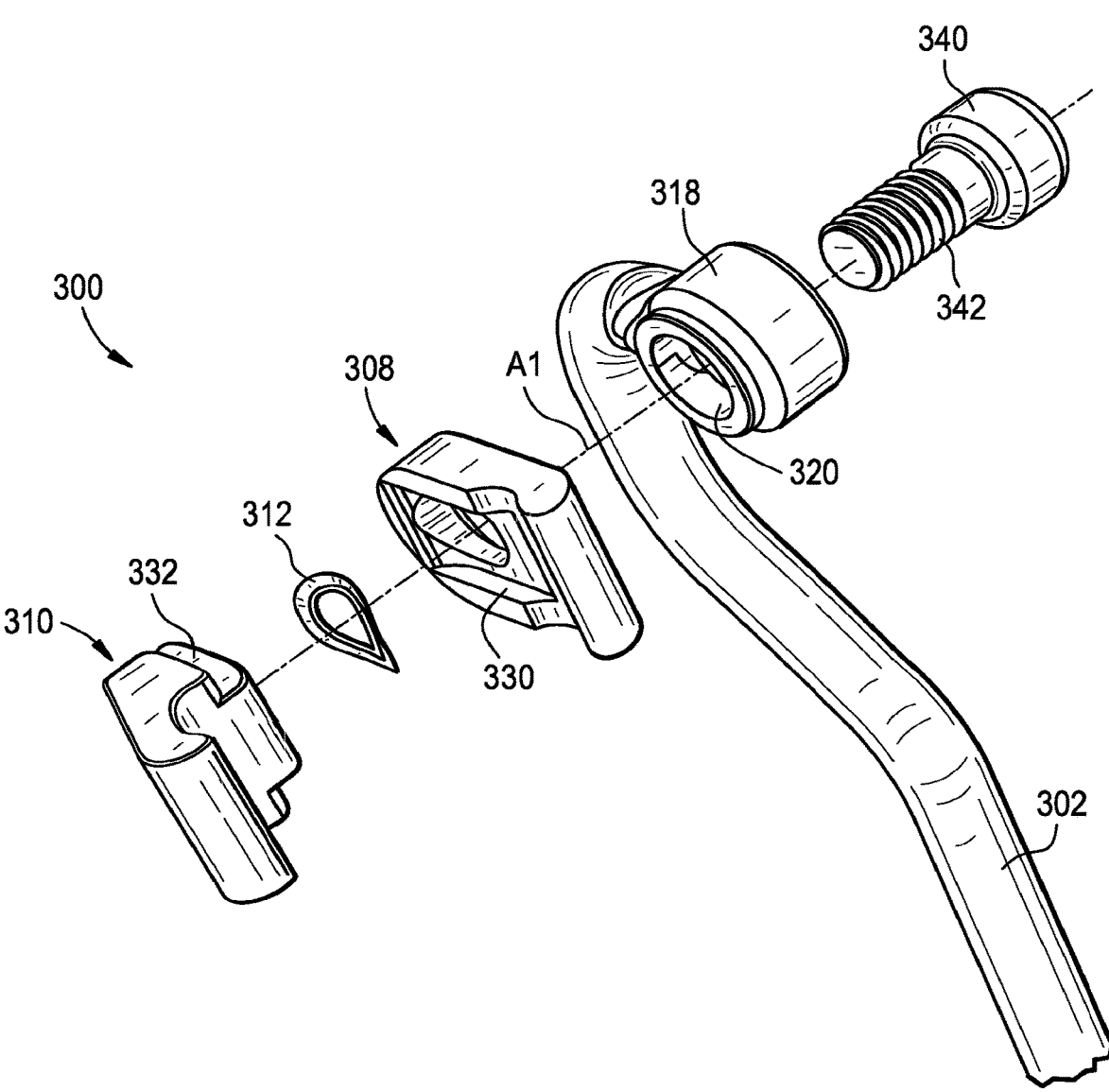
FIG. 3C is another exploded perspective view of the spinal connector of FIG. 3A.
Figure 3D:
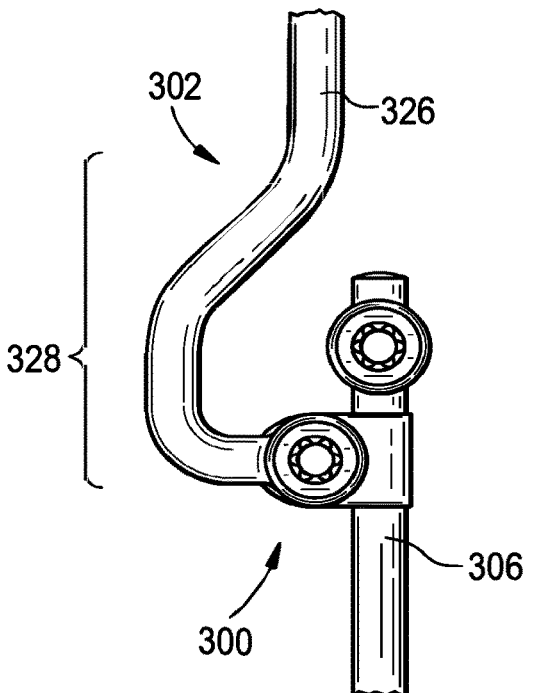
FIG. 3D is a plan view of the spinal connector of FIG. 3A coupled to a spinal fixation element.
Figure 3E:
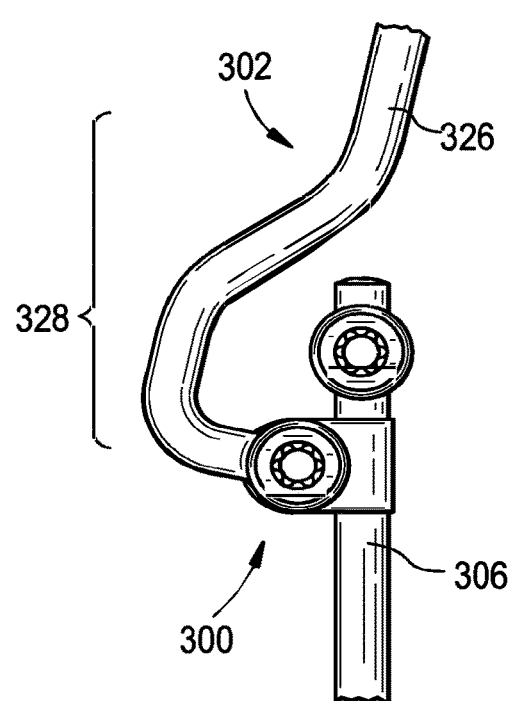
FIG. 3E is another plan view of the spinal connector of FIG. 3A coupled to a spinal fixation element.

While the illustrated recess 220 forms a portion of a cylinder, it will be appreciated that the recess can have various other shapes depending on the shape of the first spinal fixation element 206 to which the first clamping member 202 is to be coupled. For example, in the case of a first spinal fixation element 206 with a rectangular cross-section, the recess 220 can have a corresponding rectangular shape. As shown in FIG. 2H, the recess 220 can be defined by flat or planar sidewalls which, at least in some instances, can provide increased surface contact for a broader range of fixation element sizes and shapes.

As shown in FIG. 2G, the recess 220 can have a longitudinal axis A1 that extends perpendicular to a longitudinal axis A2 of the locking bolt 210 when the locking bolt extends through the first clamping member 202. Thus, the longitudinal axis A1 of the recess 220 can be perpendicular to a rotation axis A2 about which the first clamping member 202 rotates relative to the locking bolt 210. The mating portions 218 of the arms 214 can be configured to extend around any portion of the first spinal fixation element 206. In the illustrated embodiment, the arms 214 collectively extend around approximately 180 degrees of the circumference of the first spinal fixation element 206. In other embodiments, the arms 214 can cover a greater or lesser extent of the circumference of the first spinal fixation element 206. For example, the extent of coverage can be between about 90 degrees and about 270 degrees of the circumference of the first spinal fixation element 206.

Coaxial openings 226 can be formed in the opposed arms 214 of the first clamping member 202 such that the locking bolt 210 can extend through the opposed arms. The first clamping member 202 can be rotatable about a longitudinal axis A2 of the locking bolt 210 when the locking bolt is disposed through the opposed arms 214 and before the locking bolt and locking nut 212 are tightened. One or more internal dimensions of the openings 226 can be larger than corresponding external dimensions of the locking bolt 210 to allow the first clamping member 202 to translate in one or more directions relative to the locking bolt when the locking bolt is disposed through the opposed arms 214 and before the locking bolt and locking nut 212 are tightened. For example, as shown, the openings 226 can be elliptical and can have a major axis that is greater than an outside diameter of the locking bolt 210 and a minor axis that is substantially equal to the outside diameter of the locking bolt. Accordingly, the first clamping member 202 can translate relative to the locking bolt 210 only in the X and Z directions shown on the first clamping member in FIG. 2D. By way of further example, the openings 226 can be circular and can have an inside diameter that is greater than an outside diameter of the locking bolt 210 such that the first clamping member 202 can translate relative to the locking bolt in the X, Y, and Z directions shown on the first clamping member in FIG. 2D.

The second clamping member 204 can include opposed arms 228 coupled to one another at a hinge portion 230. While a living hinge 230 is shown, it will be appreciated that any of a variety of hinge mechanisms can be used. For example, the opposed arms 228 can be rotatably coupled to one another about a pivot pin. The opposed arms 228 can each include a mating portion 232 in which a recess 234 is formed for receiving a second spinal fixation element 208. Each of the opposed arms 228 can also include a main portion 236 disposed between the hinge portion 230 and the mating portion 232. The opposed arms 228 can be positionable in an unlocked position in which a slot 238 defined between the main portions 236 of the arms 228 has substantially parallel sidewalls and in which the second clamping member 204 is movable with respect to a second spinal fixation element 208 disposed between the mating portions 232 of the arms 228. The opposed arms 228 can also be positionable in a locked position in which the main portions 236 of the arms are deflected towards one another about the hinge portion 230 and in which a second spinal fixation element 208 disposed between the mating portions 232 of the arms is locked to the second clamping member 204 to resist or prevent rotation or sliding movement of the second spinal fixation element relative to the second clamping member.

The mating portions 232 can define a recess 234 therebetween sized and/or shaped according to the second spinal fixation element 208 to which the second clamping member 204 is to be coupled. For example, a diameter of the recess 234 can be substantially equal to a diameter of the second spinal fixation element 208. Alternatively, the diameter of the recess 234 can be slightly less than the diameter of the second spinal fixation element 208 to allow for a snap-fit engagement that provides tactile and/or audible feedback to the surgeon when the second clamping member 204 "snaps" onto the second spinal fixation element. As discussed further below, this feedback can be advantageous, particularly in minimally-invasive revision surgery. As another alternative, the diameter of the recess 234 can be slightly greater than that of the second spinal fixation element 208 to which the connector 200 is to be coupled, with any play being taken up by the clamping action when the locking bolt 210 and locking nut 212 are tightened. The second clamping member 204 can thus be configured to couple to second spinal fixation elements of various sizes or shapes. In some embodiments, a plurality of clamping members 204, each having recesses 234 with different sizes or shapes, can be provided as part of a kit to allow for selection of a clamping member sized and shaped appropriately for a particular application.

While the illustrated recess 234 forms a portion of a cylinder, it will be appreciated that the recess can have various other shapes depending on the shape of the second spinal fixation element 208 to which the second clamping member 204 is to be coupled. For example, in the case of a second spinal fixation element 208 with a rectangular cross-section, the recess can have a corresponding rectangular shape. As shown in FIG. 2H, the recess 234 can be defined by flat or planar sidewalls which, at least in some instances, can provide increased surface contact for a broader range of fixation element sizes and shapes.

As shown in FIG. 2G, the recess 234 can have a longitudinal axis A3 that extends perpendicular to a longitudinal axis A2 of the locking bolt 210 when the locking bolt extends through the second clamping member 204. Thus, the longitudinal axis A3 of the recess 234 can be perpendicular to a rotation axis A2 about which the second clamping member 204 rotates relative to the locking bolt 210. The mating portions 232 of the arms 228 can be configured to extend around any portion of the second spinal fixation element 208. In the illustrated embodiment, the arms 228 collectively extend around approximately 180 degrees of the circumference of the second spinal fixation element 208. In other embodiments, the arms 228 can cover a greater or lesser extent of the circumference of the second spinal fixation element 208. For example, the extent of coverage can be between about 90 degrees and about 270 degrees of the circumference of the second spinal fixation element 208.

Coaxial openings 240 can be formed in the opposed arms 228 of the second clamping member 204 such that the locking bolt 210 can extend through the opposed arms. The second clamping member 204 can be rotatable about a longitudinal axis A2 of the locking bolt 210 when the locking bolt is disposed through the opposed arms 214 and before the locking bolt and locking nut 212 are tightened. One or more internal dimensions of the openings 240 can be larger than corresponding external dimensions of the locking bolt 210 to allow the second clamping member 204 to translate in one or more directions relative to the locking bolt when the locking bolt is disposed through the opposed arms 228 and before the locking bolt and locking nut 212 are tightened. For example, as shown, the openings 240 can be elliptical and can have a major axis that is greater than an outside diameter of the locking bolt 210 and a minor axis that is substantially equal to the outside diameter of the locking bolt. Accordingly, the second clamping member 204 can translate relative to the locking bolt 210 only in the X and Z directions shown on the second clamping member in FIG. 2D. By way of further example, the openings 240 can be circular and can have an inside diameter that is greater than an outside diameter of the locking bolt 210 such that the second clamping member 204 can translate relative to the locking bolt in the X, Y, and Z directions shown on the second clamping member in FIG. 2D.

The first clamping member 202 can include a planar upper surface 242 that is configured to be substantially parallel to a planar lower surface 244 of the second clamping member 204 when the first and second clamping members are engaged with one another over the locking bolt 210. The first clamping member 202 can include a planar lower surface 246 that extends at an oblique angle with respect to the planar upper surface 242 of the first clamping member 202. The second clamping member 204 can include a planar upper surface 248 that extends at an oblique angle with respect to the planar lower surface 244 of the second clamping member 204. A spherical or ellipsoid protrusion 250 can be formed on the lower surface 246 of the first clamping member 202 and can be received in a corresponding spherical or ellipsoid recess 252 formed in the upper surface 248 of the second clamping member 204. The curved interface between the first and second clamping members 202, 204 can facilitate limited-contact, gliding movement when rotating and/or translating the first and second clamping members with respect to one another. It will be appreciated that, in some embodiments, the protrusion 250 can be formed on the second clamping member 204 and the recess 252 can be formed in the first clamping member 202.

While any of a variety of locking mechanisms can be used, in the illustrated embodiment, the locking mechanism includes a locking bolt 210 and a locking nut 212. The locking bolt 210 can include a head portion 254 and an elongate shank portion 256. The head portion 254 can have a faceted exterior surface to be gripped by a wrench to facilitate tightening or loosening of the locking bolt 210. Alternatively, or in addition, the head portion 254 can include a female recess in which a screwdriver or other instrument can be received to rotate and tighten or loosen the locking bolt 210. The shank 256 of the locking bolt 210 can be threaded along its entire length or along only a portion of its length. The threaded shank 256 can be received within the threaded interior of the locking nut 212 such that rotation of the locking bolt 210 relative to the locking nut in a first direction is effective to draw the nut towards the head portion 254 of the locking bolt and relative rotation in a second, opposite direction is effective to urge the locking nut away from the head portion of the locking bolt. At least a portion of the locking nut 212 can be non-rotatably received within the second clamping member 204. For example, the locking nut 212 can have an elliptical portion 258 configured to be received in the elliptical opening 240 of the lower arm of the second clamping member 204. The major axis of the elliptical portion 258 of the locking nut 212 can be less than the major axis of the elliptical opening 240, such that the second clamping member 204 can translate in at least one direction with respect to the locking nut when the locking nut is received therein.

The locking nut 212 can be configured to be received within the second clamping member 204 such that the locking nut sits flush or sub-flush with the lower planar surface 244 of the second clamping member or such that it sits proud as shown. While the head 254 of the locking bolt 210 is shown as sitting proud of the upper planar surface 242 of the first clamping member 202 in the illustrated embodiment, the head can be chamfered, countersunk, or otherwise configured to sit flush or sub-flush with the upper surface of the first clamping member when tightened. In some embodiments, the locking nut can be omitted and the locking mechanism can include a locking screw configured to threadably engage a threaded opening formed in one or more of the arms of the first and/or second locking members (e.g., a lower arm of the second locking member).

In use, the spinal connector 200 can be positioned in a surgical site (e.g., using a minimally-invasive technique as described in detail below). A first spinal fixation element 206 can be positioned within the recess 220 of the first clamping member 202 and a second spinal fixation element 208 can be positioned within the recess 234 of the second clamping member 204. The first and second clamping members 202, 204 can be translated and/or rotated with respect to one another and/or with respect to the locking mechanism to place the first and second spinal fixation elements 206, 208 in the desired relative alignment. The multiple degrees of freedom provided by the spinal connector 200 can be particularly advantageous when the first and second spinal fixation elements 206, 208 are not parallel to one another. As the locking bolt 210 is tightened, the first and second clamping members 202, 204 bend at their respective hinge portions 216, 230 into their respective locked configurations, clamping down on the first and second spinal fixation elements 206, 208 and locking them to the connector 200. At the same time, the first and second clamping members 202, 204 are squeezed into firm engagement with one another, resisting or preventing the first and second clamping members from rotating with respect to one another and/or from translating in one or more directions with respect to one another. Actuation of a single locking mechanism can thus be effective to (1) lock the first clamping member to a first spinal fixation element, (2) lock the second clamping member to a second spinal fixation element, (3) lock a rotational degree of freedom between the first and second clamping members, and (4) lock one or more translational degrees of freedom between the first and second clamping members. This multiple functionality of locking onto multiple spinal fixation elements and locking one or more degrees of freedom of the connector can be particularly advantageous in minimally-invasive surgery, as access is only required to a single locking mechanism and two or more functions can be performed in a single step.

The spinal connector 200 can be coupled to the spinal fixation elements 206, 208 in any of a variety of orientations. For example, the spinal connector 200 can be coupled to first and second spinal fixation elements 206, 208 that substantially lie in a common coronal plane such that the locking bolt 210 extends along an anterior-posterior or sagittal axis of the patient. By way of further example, the spinal connector 200 can be coupled to first and second spinal fixation elements 206, 208 that substantially lie in a common sagittal plane such that the locking bolt extends along a medial-lateral or transverse axis of the patient. The spinal connector 200 can also be coupled to the spinal fixation elements 206, 208 in any orientation between the above two examples and at any point along the lengths of the spinal fixation elements. The first and second spinal fixation elements 206, 208 need not lie in a common plane.

In the illustrated embodiment, the first and second spinal fixation elements 206, 208 are elongate spinal rods, though it will be appreciated that any of a variety of fixation elements can be used instead or in addition, such as bone plates. The first and second spinal fixation elements 206, 208 can be completely straight or can include one or more bends, curves, joints, offsets, jogs, etc. as described above.

FIGS. 3A-3E illustrate another exemplary embodiment of a spinal connector 300. The connector 300 generally includes a first spinal fixation element 302 and a connection assembly 304 for coupling the first spinal fixation element 302 to a second spinal fixation element 306. The second spinal fixation element 306 can be a previously-implanted spinal fixation element to which the connector 300 is to be coupled or can be implanted with the connector 300 or as part of the same procedure as the connector 300. The connection assembly 304 can include a locking mechanism for selectively locking an orientation of the first spinal fixation element 302 relative to the connection assembly 304 and for locking a position and an orientation of the connection assembly relative to the second spinal fixation element 306. As shown, the connection assembly 304 can include an upper clamping arm 308, a lower clamping arm 310, a biasing element 312, and a locking element 314.

In the illustrated embodiment, the first and second spinal fixation elements 302, 306 are elongate spinal rods, though it will be appreciated that any of a variety of fixation elements can be used instead or in addition, such as bone plates. The first spinal fixation element 302 can include a mating feature 318 formed on or coupled to a first terminal end thereof configured to rotatably couple the first spinal fixation element to the connection assembly 304. In the illustrated embodiment, the mating feature 318 is a ring-shaped structure formed integrally with the first spinal fixation element 302. The mating feature 318 can include a central opening 320 configured to receive the locking element therethrough such that a non-threaded portion of the locking element is disposed in the central opening 320 and the first spinal fixation element 302 is freely rotatable about the locking element until the locking element is tightened (e.g., rotatable about a longitudinal axis of the locking element). Stated differently, the connection assembly 304 can be rotatable about a longitudinal axis A1 of the central opening 320. A second, opposite terminal end 324 of the first spinal fixation element 302 can be configured to facilitate minimally-invasive insertion of the first spinal fixation element. For example, the second terminal end 324 can be rounded, bulleted, tapered, etc. to allow for atraumatic tunneling of the first spinal fixation element 302 subcutaneously from an insertion portal to a final implanted position.

The first spinal fixation element 302 can be completely straight or can include one or more bends, curves, joints, offsets, jogs, etc. For example, the first spinal fixation element 302 can have an S-shaped or Z-shaped bend to provide clearance for patient anatomy or for a portion (e.g., a bone screw) of a fixation construct to which the connector 300 is to be coupled. In the illustrated embodiment, the first spinal fixation element 302 includes a straight portion 326 joined by a curved portion 328 to the mating feature 318. The curved portion 328 can provide an offset such that the first spinal fixation element 302 can bend around a portion of the patient's anatomy or a portion of a fixation construct to which the connector 300 is coupled. Accordingly, a low-profile construct can be formed, with the straight portion 326 of the first spinal fixation element 302 positioned as a natural extension of the second spinal fixation element 306. It will thus be appreciated that the connector 300 can be clamped onto a previously-installed second spinal fixation element 306, intermediate to first and second bone anchors securing the second spinal fixation element, without the first spinal fixation element 302 interfering with the bone anchors. The first spinal fixation element 302 can be rigid, can be bendable or malleable, or can include both rigid portions and bendable portions. Thus, in some embodiments, the contour of the first spinal fixation element 302 can be adjusted as needed for a particular procedure, either manually or with the assistance of bending tools.

The upper clamping arm 308 can include a rectangular recess 330 in which a corresponding rectangular protrusion 332 formed on the lower clamping arm 310 can be received such that the upper and lower clamping arms are hinged together and can pivot relative to one another. It will be appreciated that, in other embodiments, the above arrangement can be reversed such that the lower clamping arm 310 includes the recess 330 and the upper clamping arm 308 includes the protrusion 332.

Each of the upper and lower clamping arms 308, 310 can also include a mating portion 334 for receiving the second spinal fixation element 306. Together, the mating portions 334 of the upper and lower clamping arms 308, 310 can define a recess 336 therebetween sized and/or shaped according to the second spinal fixation element 306 to which the connector 300 is to be coupled. For example, a diameter of the recess 336 can be substantially equal to a diameter of the second spinal fixation element 306. Alternatively, the diameter of the recess 336 can be slightly less than the diameter of the second spinal fixation element 306 to allow for a snap-fit engagement that provides tactile and/or audible feedback to the surgeon when the connector 300 "snaps" onto the second spinal fixation element 306. As discussed further below, this feedback can be advantageous, particularly in minimally-invasive revision surgery. As another alternative, the diameter of the recess 336 can be slightly greater than that of the second spinal fixation element 306, with any play being taken up by the clamping action when the locking element 314 is tightened. The connector 300 can thus be configured to couple to second spinal fixation elements of various sizes or shapes. In some embodiments, a plurality of connectors 300, each having recesses 336 with different sizes or shapes, can be provided as part of a kit to allow for selection of a connector sized and shaped appropriately for a particular application.

While the illustrated recess 336 forms a portion of a cylinder, it will be appreciated that the recess can have various other shapes depending on the shape of the second spinal fixation element 306 to which the connector 300 is to be coupled. For example, in the case of a second spinal fixation element 306 with a rectangular cross-section, the recess 336 can have a corresponding rectangular shape.

The recess 336 can have a longitudinal axis A2 that extends perpendicular to the longitudinal axis A1 of the central opening 320 and perpendicular to a longitudinal axis of the locking element 314. Thus, the longitudinal axis A2 of the recess 336 can be perpendicular to a rotation axis about which the first spinal fixation element 302 rotates relative to the connection assembly 304. In such embodiments, when a second spinal fixation element 306 is received in the recess 336, the first spinal fixation element 302 can be rotatable about an axis perpendicular to a longitudinal axis of the second spinal fixation element 306. The mating portions 334 of the upper and lower clamping arms 308, 310 can be configured to extend around any portion of the second spinal fixation element 306. In the illustrated embodiment, the clamping arms 308, 310 collectively extend around approximately 240 degrees of the circumference of the second spinal fixation element 306. In other embodiments, the clamping arms 308, 310 can cover a greater or lesser extent of the circumference of the second spinal fixation element 306. For example, the extent of coverage can be between about 90 degrees and about 270 degrees of the circumference of the second spinal fixation element 306.

The biasing element 312 can be disposed between the upper and lower clamping arms 308, 310 and can be configured to bias the arms towards a clamped or partially clamped position. Accordingly, the diameter of the recess 336 defined between the arms 308, 310 can increase as the arms are spread apart against the bias of the biasing element 312 when a spinal fixation element 306 is inserted through an open end of the clamp. Once the spinal fixation element 306 clears the leading ends of the arms 308, 310 and is fully-disposed within the recess 336, the biasing element 312 can cause the hinged portion of the arms to spread apart, closing the mating portions 334 of the arms around the spinal fixation element, thereby providing a "snap fit" engagement with tactile and/or audible feedback to the user.

In the illustrated embodiment, the biasing element is a wave spring or washer 312. The washer 312 can be bent in one or more planes and can include a central opening through which the locking element 314 can be received. The washer 312 can be formed from a flexible and resilient material configured to deform to the shape of a flat washer when an external force (e.g., the force of the spinal fixation element 306 being introduced into the open end of the clamp) is applied and to spring back to the wave shape shown in FIG. 3B when the external force is removed.

The upper and lower clamping arms 308, 310 can include openings 338 that are coaxial with one another and with the central opening of the biasing element 312 such that the locking element 314 can extend through the clamping arms and through the biasing element.

While any of a variety of locking elements can be used, in the illustrated embodiment, the locking element is a locking screw 314. The locking screw 314 can include a head portion 340 and an elongate shank portion 342. The head portion 340 can include a driving interface (e.g., a female recess 344 in which a screwdriver or other instrument can be received) to facilitate rotation and tightening or loosening of the locking screw 314. The shank 342 of the locking screw 314 can be threaded along its entire length or along only a portion of its length. In some embodiments, a section of the shank 342 immediately distal to the head portion 340 can be left unthreaded to allow the mating feature 318 of the first spinal fixation element 302 to rotate freely about the locking screw 314 until the locking screw is tightened. At least a portion of the opening 338 formed in the lower clamping arm 310 can be threaded and can be configured to threadably engage a threaded portion of the shank 342. Accordingly, rotation of the locking screw 314 relative to the lower clamping arm 310 in a first direction can be effective to draw the upper and lower clamping arms 308, 310 together and relative rotation in a second, opposite direction can be effective to allow the upper and lower clamping arms to move apart (e.g., under the bias of the biasing element 312). The mating feature 318 of the first spinal fixation element 302 can include a recess 346 sized to receive the head 340 of the locking screw 314 such that the locking screw is countersunk in the mating feature.

The connector 300 can be positionable in an unlocked configuration in which the locking screw 314 is not tightened, the upper and lower clamping arms 308, 310 are movable with respect to the second spinal fixation element 306 disposed between the mating portions thereof, and the first spinal fixation element 302 is freely rotatable about the locking screw. The connector 300 can also be positionable in a locked configuration by tightening the locking screw 314 such that a second spinal fixation element 306 disposed between the mating portions of the arms 308, 310 is locked to resist or prevent rotation or sliding movement of the second spinal fixation element 306 relative to the connector 300 and such that the first spinal fixation element 302 is not freely rotatable relative to the connection assembly 304.

In use, the spinal connector 300 can be positioned in a surgical site (e.g., using a minimally-invasive technique as described in detail below). A previously-placed second spinal fixation element 306 can be positioned within the recess 336 defined between the upper and lower clamping arms 308, 310 and the connection assembly 304 can be moved to a desired position and/or orientation with respect to the second spinal fixation element 306. In addition, the first spinal fixation element 302 can be rotated to a desired position. As the locking element 314 is tightened, the upper and lower clamping arms 308, 310 can clamp down on the second spinal fixation element 306 to clamp the connection assembly 304 thereto and lock the position and orientation of the connection assembly relative to the second spinal fixation element. At the same time or at substantially the same time, the mating feature 318 of the first spinal fixation element 302 can be squeezed into firm engagement with the upper clamping arm 308 to lock the rotational position of the first spinal fixation element 302 relative to the connection assembly 304. Actuation of a single locking mechanism can thus be effective to (1) lock an orientation of a first spinal fixation element relative to the connection assembly and (2) lock a position and an orientation of the connector relative to a second spinal fixation element. This multiple functionality of locking onto a second spinal fixation element and locking one or more degrees of freedom of the connector can be particularly advantageous in minimally-invasive surgery, as access is only required to a single locking mechanism and two or more functions can be performed in a single step.

The spinal connector 300 can be coupled to the second spinal fixation element 306 in any of a variety of orientations. For example, the spinal connector 300 can be coupled to the second spinal fixation element 306 such that the driving interface 344 of the locking screw 314 faces in a posterior direction relative to the patient and such that the locking screw is advanced along an anterior-posterior axis to lock the connector. By way of further example, the spinal connector 300 can be coupled to the second spinal fixation element 306 such that the driving interface 344 of the locking screw 314 faces in a medial or lateral direction relative to the patient and the locking screw is advanced along a medial-lateral axis to lock the connector. The spinal connector 300 can also be coupled to the second spinal fixation element 306 in any orientation between the above two examples and at any point along a length of the second spinal fixation element.

FIGS. 4A-4E illustrate another exemplary embodiment of a spinal connector 400. The connector 400 generally includes a first spinal fixation element 402 and a connection assembly 404 for coupling the first spinal fixation element 402 to a second spinal fixation element 406. The second spinal fixation element 406 can be a previously-implanted spinal fixation element to which the connector 400 is to be coupled or can be implanted with the connector 400 or as part of the same procedure as the connector 400. The connection assembly 404 can include a locking mechanism for selectively locking an orientation of the first spinal fixation element 402 relative to the connection assembly 404 and for locking a position and an orientation of the connection assembly relative to the second spinal fixation element 406. As shown, the connection assembly 404 can include a clamping member 408, a washer 410, and a locking element 412.

In the illustrated embodiment, the first and second spinal fixation elements 402, 406 are elongate spinal rods, though it will be appreciated that any of a variety of fixation elements can be used instead or in addition, such as bone plates. The first spinal fixation element 402 can include a mating feature 418 formed on or coupled to a first terminal end thereof configured to rotatably couple the first spinal fixation element to the connection assembly 404. In the illustrated embodiment, the mating feature 418 is a ring-shaped structure formed integrally with the first spinal fixation element 402. The mating feature 418 can include a central opening 420 configured to receive a stud portion 414 of the clamping member 408 therethrough such that the mating feature is rotatable about the stud portion (e.g., about a longitudinal axis of the stud portion) until the locking element 412 is tightened. Stated differently, the clamping member 408 can be rotatable about a longitudinal axis A1 of the central opening 420. The clamping member 408 can also be rotatable about a transverse axis A2 of the central opening 420. In particular, the central opening 420 can be configured to allow positioning of the stud portion 414 therein at a plurality of angles. Thus, the stud portion 414 can be disposed in the central opening 420 such that a longitudinal axis of the stud portion is collinear with a longitudinal axis of the central opening, or such that the longitudinal axis of the stud portion extends at an oblique angle with respect to the longitudinal axis of the central opening. To facilitate such positioning, for example, the central opening 420 can be elongated in one or more directions such that the central opening is non-circular. By way of further example, the central opening 420 can include one or more lateral reliefs or cut-outs 416 to allow for angulation of the stud portion 414 within the central opening 420.

A second, opposite terminal end 424 of the first spinal fixation element 402 can be configured to facilitate minimally-invasive insertion of the first spinal fixation element. For example, the second terminal end 424 can be rounded, bulleted, tapered, etc. to allow for atraumatic tunneling of the first spinal fixation element 402 subcutaneously from an insertion portal to a final implanted position.

The first spinal fixation element 402 can be completely straight or can include one or more bends, curves, joints, offsets, jogs, etc. For example, the first spinal fixation element 402 can have an S-shaped or Z-shaped bend to provide clearance for patient anatomy or for a portion (e.g., a bone screw 422) of a fixation construct to which the connector 400 is to be coupled. In the illustrated embodiment, the first spinal fixation element 402 includes a straight portion 426 joined by a curved portion 428 to another straight portion 430 where the mating feature 418 is formed. The curved portion 428 can provide an offset such that the first spinal fixation element 402 can bend around a portion of the patient's anatomy or a portion of a fixation construct to which the connector 400 is coupled. Accordingly, a low-profile construct can be formed, with the straight portion 426 of the first spinal fixation element 402 positioned as a natural extension of the second spinal fixation element 406. It will thus be appreciated that the connector 400 can be clamped onto a previously-installed second spinal fixation element 406, intermediate to first and second bone anchors securing the second spinal fixation element, without the first spinal fixation element 402 interfering with the bone anchors. The first spinal fixation element 402 can be rigid, can be bendable or malleable, or can include both rigid portions and bendable portions. Thus, in some embodiments, the contour of the first spinal fixation element 402 can be adjusted as needed for a particular procedure, either manually or with the assistance of bending tools.

Figure 4A:
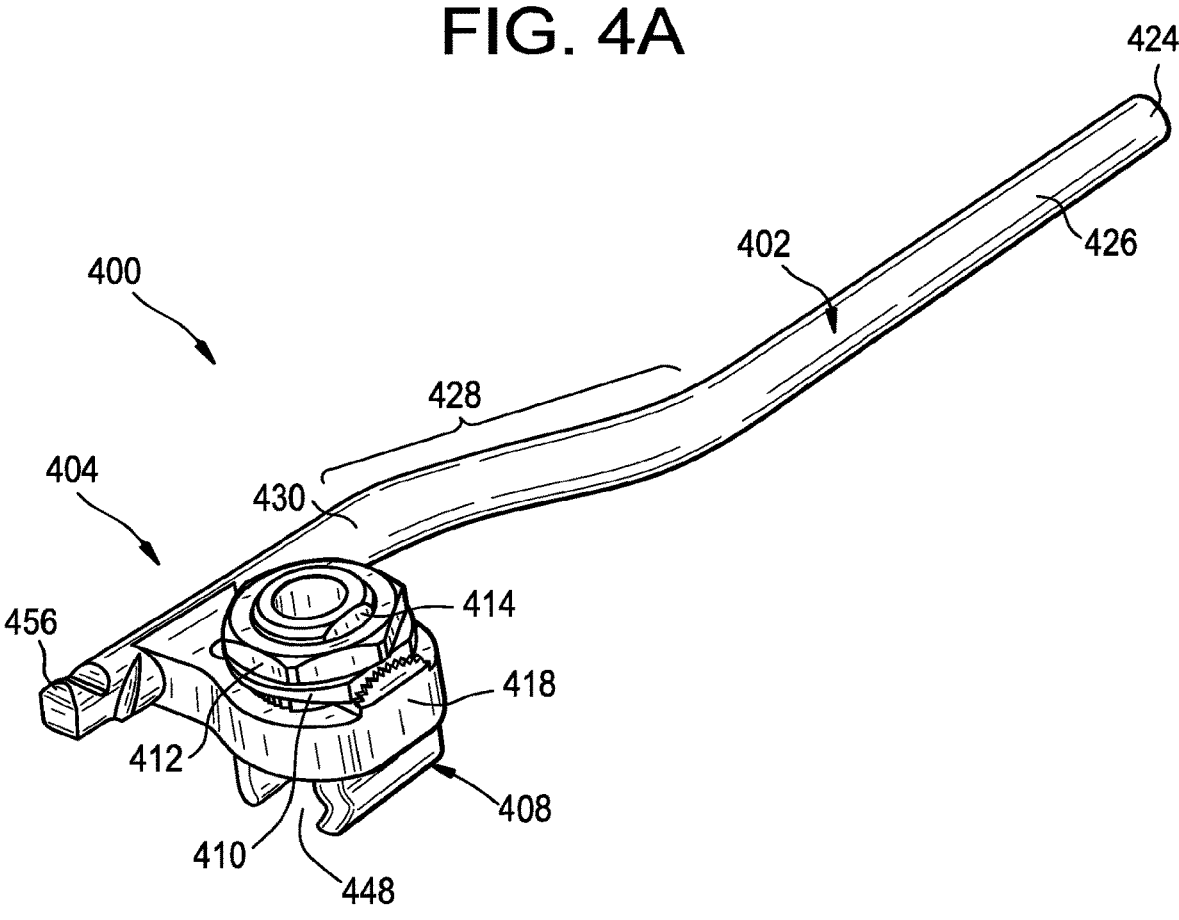
FIG. 4A is a perspective view of another spinal connector.
Figure 4B:
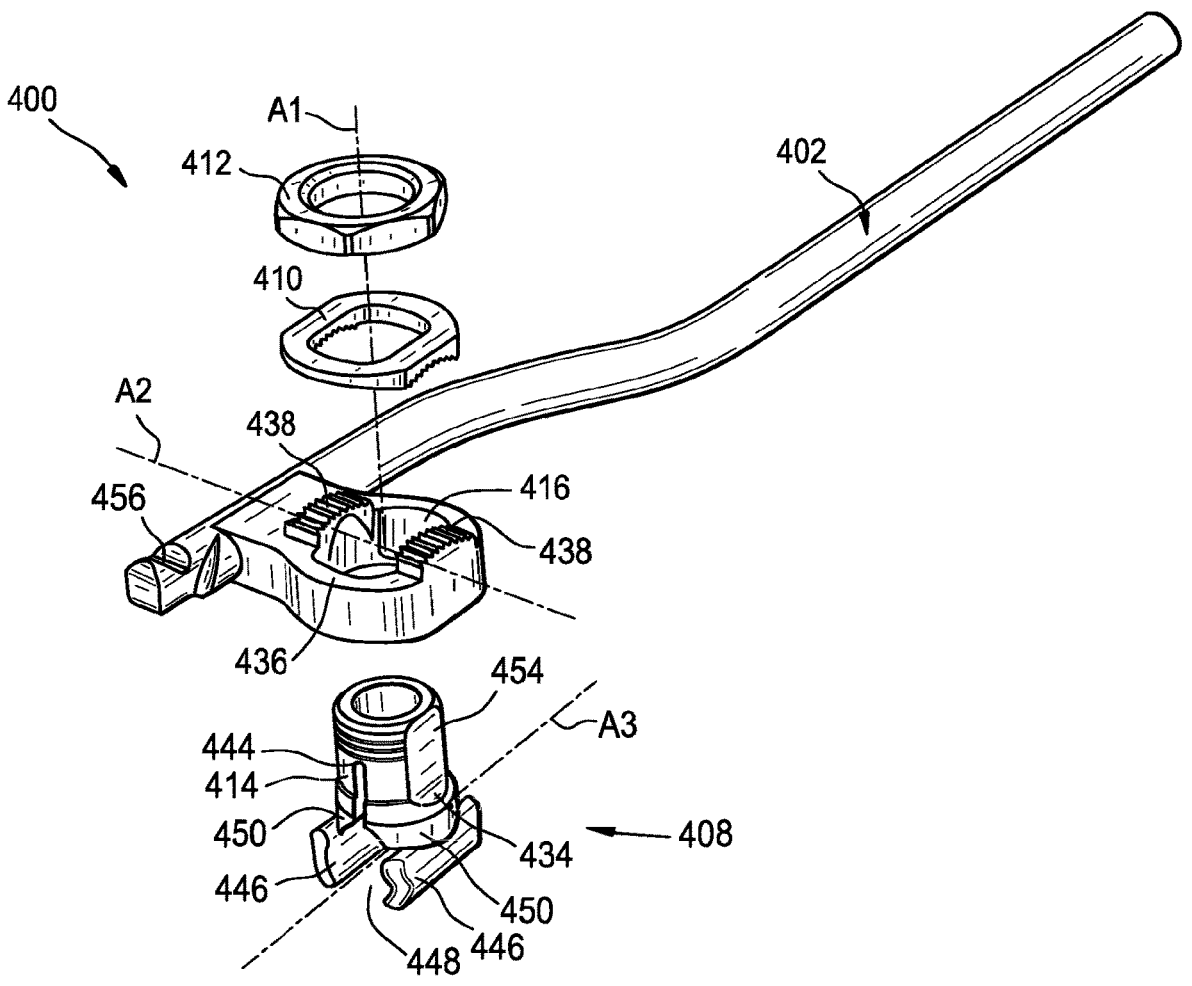
FIG. 4B is an exploded perspective view of the spinal connector of FIG. 4A.
Figure 4C:
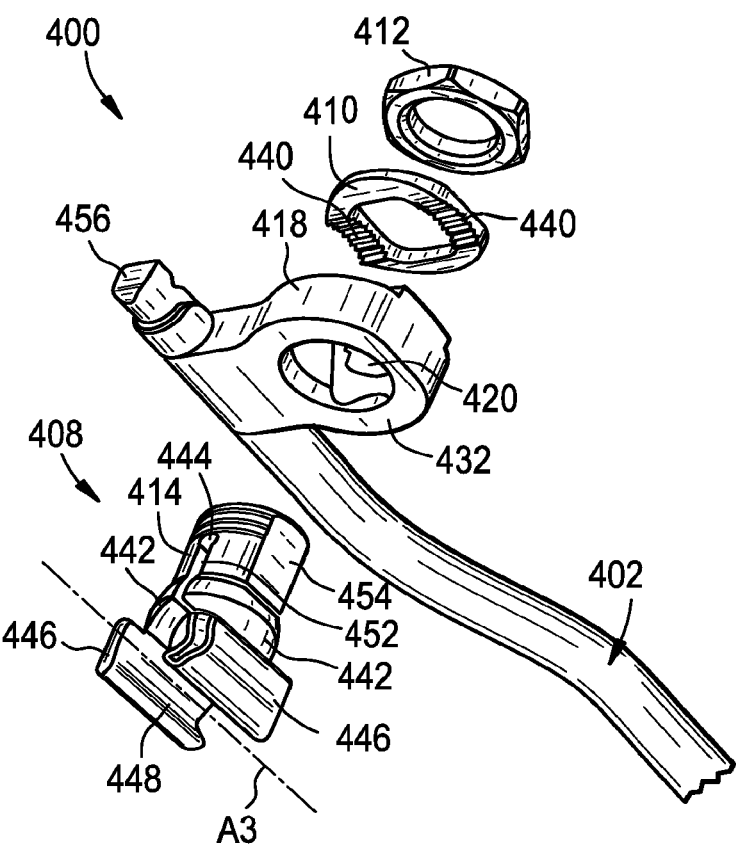
FIG. 4C is another exploded perspective view of the spinal connector of FIG. 4A.
Figure 4D:
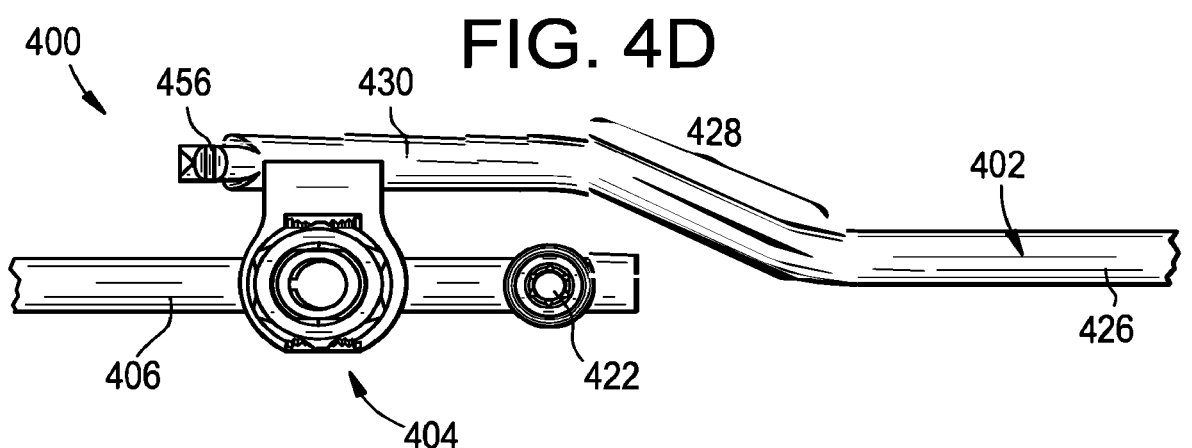
FIG. 4D is a plan view of the spinal connector of FIG. 4A coupled to a spinal fixation element.

As shown in FIGS. 4B-4C, the mating feature 418 can include a lower surface 432 configured to engage a shoulder 434 formed on the clamping member 408 and an upper surface 436 configured to engage the washer 410. The upper surface 436 can include one or more surface features that can be engaged by corresponding surface features of the washer 410 to lock a relative angle between the stud portion 414 of the clamping member 408 and the mating feature 418 about the transverse axis A2 of the central opening. In the illustrated embodiment, the surface features include first and second cylindrical protrusions 438 with a plurality of teeth formed thereon. While teeth are shown, it will be appreciated that any of a variety of surface features can be used, such as ratchet steps, roughened or textured contact surfaces, etc. The teeth of the protrusions 438 can mesh with corresponding teeth formed in recesses 440 of the washer 410 in which the protrusions can be received. The teeth can extend radially-outward from the pivot axis A2 about which the mating feature 418 can rotate relative to the stud portion 414 when the stud portion is disposed within the central opening 420 of the mating feature. It will be appreciated that, in other embodiments, the protrusions 438 can be formed on the washer 410 and the recesses 440 can be formed in the mating feature 418.

The clamping member 408 can include opposed arms 442 coupled to one another at a hinge portion 444. While a living hinge 444 is shown, it will be appreciated that any of a variety of hinge mechanisms can be used. For example, the opposed arms 442 can be rotatably coupled to one another about a pivot pin. The opposed arms 442 can each include a mating portion 446 for receiving the second spinal fixation element 406. Each of the opposed arms 442 can also include a main portion 450 disposed between the hinge portion 444 and the mating portion 446. The opposed arms 442 can be positionable in an unlocked position in which a slot 452 formed between the main portions 450 of the arms has substantially parallel sidewalls and in which the clamping member 408 is movable with respect to a second spinal fixation element 406 disposed between the mating portions 446 of the arms. The opposed arms 442 can also be positionable in a locked position in which the main portions 450 of the arms are deflected towards one another about the hinge portion 444 and in which a second spinal fixation element 406 disposed between the mating portions 446 of the arms is locked to the clamping member 408 to resist or prevent rotation or sliding movement of the second spinal fixation element 406 relative to the clamping member 408. The outer sidewalls 454 of the arms 442 can be tapered such that advancing the locking element 412 distally towards the shoulder 434 of the clamping member 408 squeezes the arms together, moving them towards the locked position. The hinge portions 444 of the arms 442 can be resilient such that retracting the locking element 412 proximally away from the shoulder 434 of the clamping member 408 allows the arms to spread apart and move towards the unlocked position.

The mating portions 446 can define a recess 448 therebetween sized and/or shaped according to the spinal fixation element to which the clamping member 408 is to be coupled. For example, a diameter of the recess 448 can be substantially equal to a diameter of the second spinal fixation element 406. Alternatively, the diameter of the recess 448 can be slightly less than the diameter of the second spinal fixation element 406 to allow for a snap-fit engagement that provides tactile and/or audible feedback to the surgeon when the clamping member 408 "snaps" onto the second spinal fixation element 406. As discussed further below, this feedback can be advantageous, particularly in minimally-invasive revision surgery. As another alternative, the diameter of the recess 448 can be slightly greater than that of the second spinal fixation element 406, with any play being taken up by the clamping action when the locking element 412 is tightened. The clamping member 408 can thus be configured to couple to spinal fixation elements of various sizes or shapes. In some embodiments, a plurality of clamping members 408, each having recesses 448 with different sizes or shapes, can be provided as part of a kit to allow for selection of a clamping member sized and shaped appropriately for a particular application.

While the illustrated recess 448 forms a portion of a cylinder, it will be appreciated that the recess can have various other shapes depending on the shape of the second spinal fixation element 406 to which the connector 400 is to be coupled. For example, in the case of a second spinal fixation element 406 with a rectangular cross-section, the recess 448 can have a corresponding rectangular shape.

The recess 448 can have a longitudinal axis A3 that extends perpendicular to a longitudinal axis of the stud portion 414 and to the longitudinal axis of the locking element 412. Thus, the longitudinal axis A3 of the recess 448 can be perpendicular to an axis along which the locking element 412 is advanced. The mating portions 448 of the arms 442 can be configured to extend around any portion of the second spinal fixation element 406. In the illustrated embodiment, the arms 442 collectively extend around approximately 240 degrees of the circumference of the second spinal fixation element 406. In other embodiments, the arms can cover a greater or lesser extent of the circumference of the second spinal fixation element 406. For example, the extent of coverage can be between about 90 degrees and about 270 degrees of the circumference of the second spinal fixation element 406.

While any of a variety of locking elements can be used, in the illustrated embodiment, the locking element comprises a locking nut 412. At least a portion of the locking nut 412 can include a thread configured to threadably engage a corresponding thread formed on the stud portion 414 of the clamping member 408. Accordingly, rotation of the locking nut 412 relative to the stud portion 414 in a first direction can be effective to urge the locking nut towards the shoulder portion 434 of the clamping member 408, compressing the washer 410 and the mating feature 418 therebetween, and relative rotation in a second, opposite direction can be effective to move the locking nut away from the shoulder portion of the clamping member.

The connector 400 can be positionable in an unlocked configuration in which the locking nut 412 is not tightened, the mating feature 418 and the first spinal fixation element 402 are rotatable about the axis A1 and the axis A2 relative to the stud portion 414 of the clamping member 408, and the clamping member is rotatable and slidable with respect to a second spinal fixation element 406 disposed between the mating portions 446 thereof. The connector 400 can also be positionable in a locked configuration by tightening the locking nut 412 such that a second spinal fixation element 406 disposed between the mating portions 446 is locked to resist or prevent rotation or sliding movement of the second spinal fixation element relative to the connector 400 and such that the mating feature 418 and the first spinal fixation element 402 are not freely rotatable relative to the stud portion 414 about the axis A1 or the axis A2.

In use, the spinal connector 400 can be positioned in a surgical site (e.g., using a minimally-invasive technique as described in detail below). A previously-placed second spinal fixation element 406 can be positioned within the recess 448 defined between the arms 442 of the clamping member 408 and the clamping member can be moved to a desired position and/or orientation with respect to the second spinal fixation element 406. In addition, the first spinal fixation element 402 can be rotated to a desired position about the axis A1 and/or the axis A2. As the locking element 412 is tightened, the arms 442 can clamp down on the second spinal fixation element 406 to lock the position and orientation of the clamping member 408 relative to the second spinal fixation element. At the same time, the mating feature 418 of the first spinal fixation element 402 can be squeezed into firm engagement with the shoulder 434 of the clamping member 408 and the teeth of the washer 410, resisting or preventing the first spinal fixation element 402 from rotating about the axis A1 or the axis A2 with respect to the stud portion 414. Actuation of a single locking mechanism can thus be effective to (1) lock the position and orientation of the connector relative to a second spinal fixation element and (2) lock first and second rotational degrees of freedom of the first spinal fixation element relative to the second spinal fixation element. This multiple functionality of locking onto a second spinal fixation element and locking one or more degrees of freedom of the connector can be particularly advantageous in minimally-invasive surgery, as access is only required to a single locking mechanism and two or more functions can be performed in a single step.

The spinal connector 400 can be coupled to the second spinal fixation element 406 in any of a variety of orientations. For example, the spinal connector 400 can be coupled to the second spinal fixation element 406 such that the longitudinal axis of the stud portion 414 extends in an anterior-posterior direction relative to the patient. By way of further example, the spinal connector 400 can be coupled to the second spinal fixation element 406 such that the longitudinal axis of the stud portion extends in a medial-lateral direction relative to the patient. The spinal connector 400 can also be coupled to the second spinal fixation element 406 in any orientation between the above two examples and at any point along a length of the second spinal fixation element.

Figure 4E:
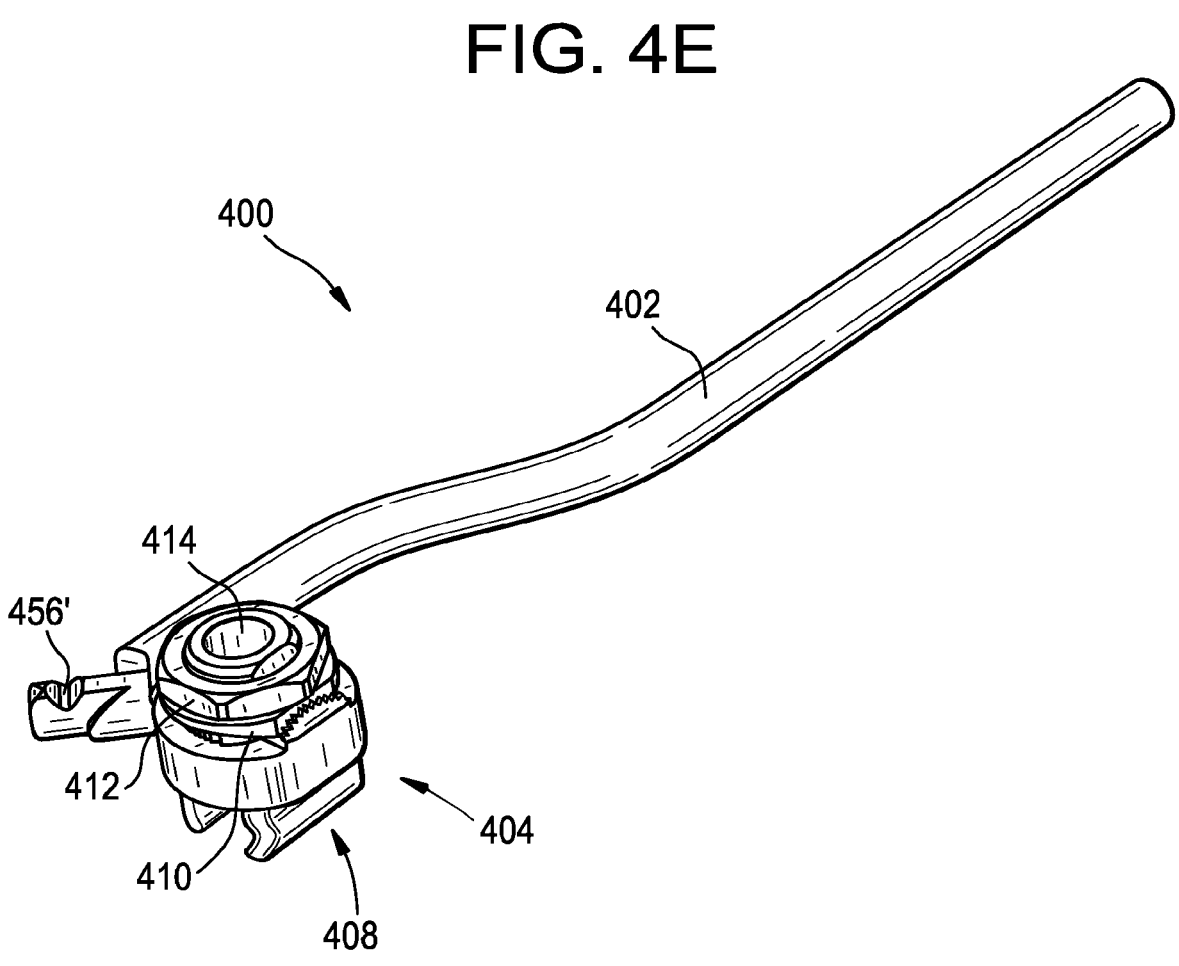
FIG. 4E is a perspective view of the spinal connector of FIG. 4A with an alternative coupling feature.

The first spinal fixation element 406 can include one or more coupling features for attaching the first spinal fixation element to an insertion instrument. For example, the first spinal fixation element 402 can include a coupling feature 456 that extends along a longitudinal axis of the straight portion 430, as shown in FIG. 4A. By way of further example, the first spinal fixation element 402 can include a coupling feature 456' that extends at an oblique angle with respect to a longitudinal axis of the straight portion 430, as shown in FIG. 4E. While not shown, the spinal connectors 100, 200, 300 described above can include a similar coupling feature.

Figure 5A:
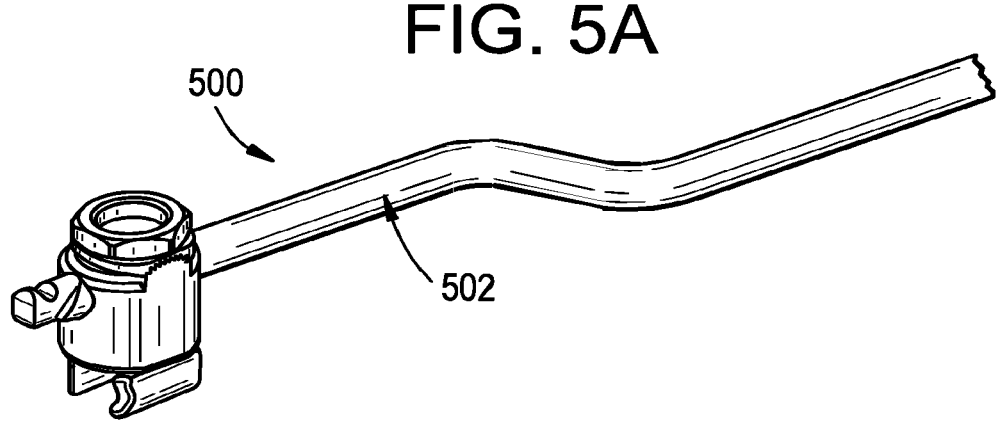
FIG. 5A is a perspective view of another spinal connector.
Figure 5B:
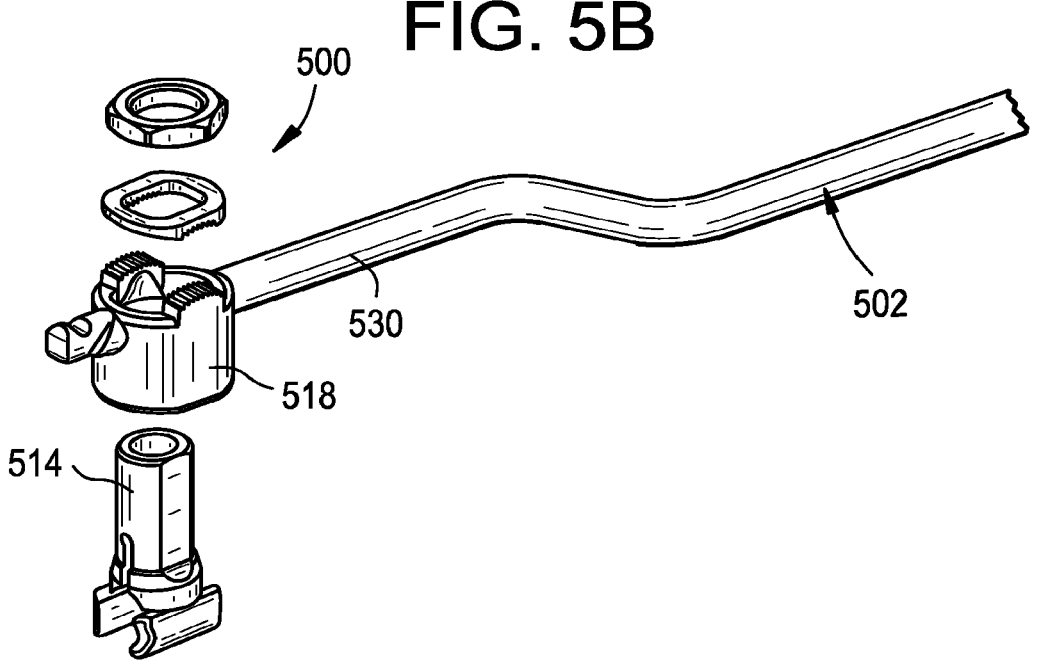
FIG. 5B is an exploded perspective view of the spinal connector of FIG. 5A.
Figure 5C:
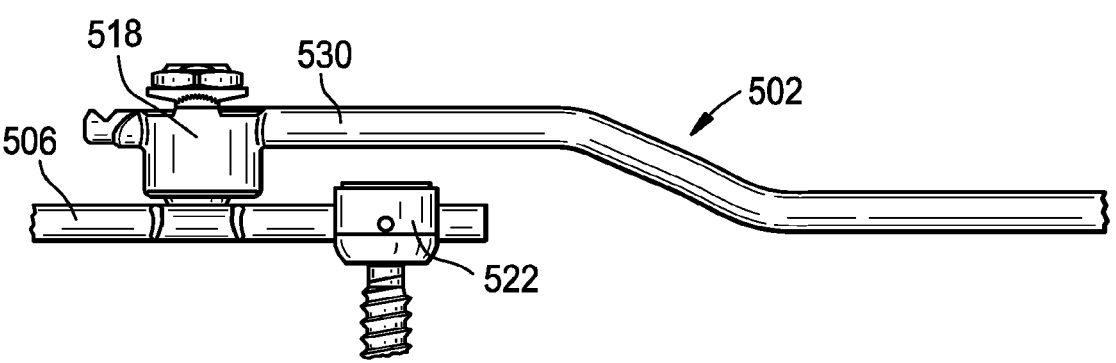
FIG. 5C is a profile view of the spinal connector of FIG. 5A coupled to a spinal fixation element.
Figure 5D:
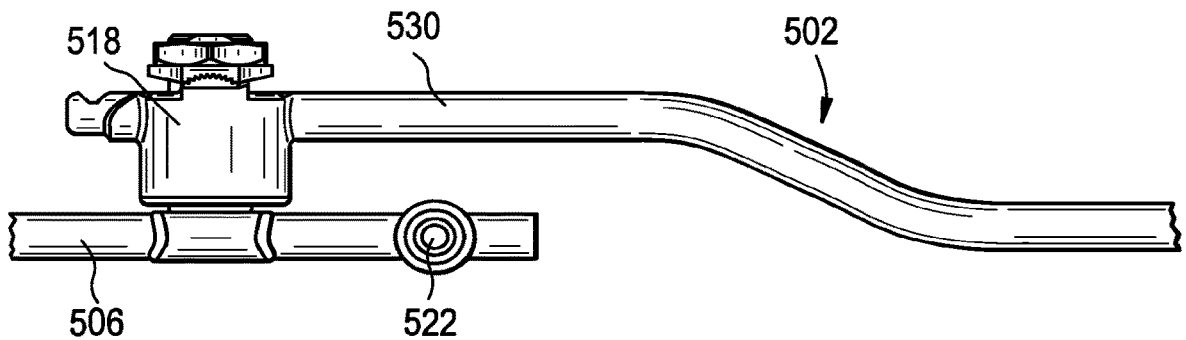
FIG. 5D is a plan view of the spinal connector of FIG. 5A coupled to a spinal fixation element in another orientation.

FIGS. 5A-5D illustrate another exemplary embodiment of a spinal connector 500. Except as indicated below, the structure and operation of the spinal connector 500 is substantially identical to that of the spinal connector 400 discussed above. Accordingly, a detailed description of said structure and operation is omitted here for the sake of brevity. The mating feature 518 of the spinal connector 500 is disposed in-line with the adjacent rod portion 530, as opposed to extending laterally therefrom as in the spinal connector 400. This can allow the connector 500 to be positioned such that the second spinal fixation element 506 is disposed directly beneath the first spinal fixation element 502, as shown in FIG. 5C. The connector 500 can also be positioned with respect to the second spinal fixation element 506 as shown in FIG. 5D, such that the longitudinal axis of the mating feature 518 is perpendicular to the longitudinal axis of a bone anchor 522 coupled to the second spinal fixation element.

In addition, the mating feature 518 and the stud portion 514 of the clamping member 508 are taller in the spinal connector 500 than in the spinal connector 400. This can provide sufficient clearance space for the first spinal fixation element 502 to extend over a bone anchor 522 holding the second spinal fixation element 506 in place without the first spinal fixation element interfering with the bone anchor.

FIGS. 6A-6G schematically illustrate a method of using a spinal connector of the type disclosed herein to extend a fixation construct to an adjacent vertebral level as part of a minimally-invasive revision surgery.

FIG. 6A illustrates a portion of a spinal column of a patient in which a first spinal fixation element (e.g., an elongate fixation rod R1) has been coupled to a superior vertebra V1 and an adjacent inferior vertebra V2 using pedicle screws S1, S2. The fixation construct is implanted beneath the patient's skin D.

As shown in FIG. 6B, a first minimally invasive pathway P1 can be formed to access a third vertebra V3 inferior to the vertebra V2 and adjacent to the vertebra V2. In some embodiments, a percutaneous access device can be used to provide the minimally-invasive pathway P1.

Figures 6C, 6D:
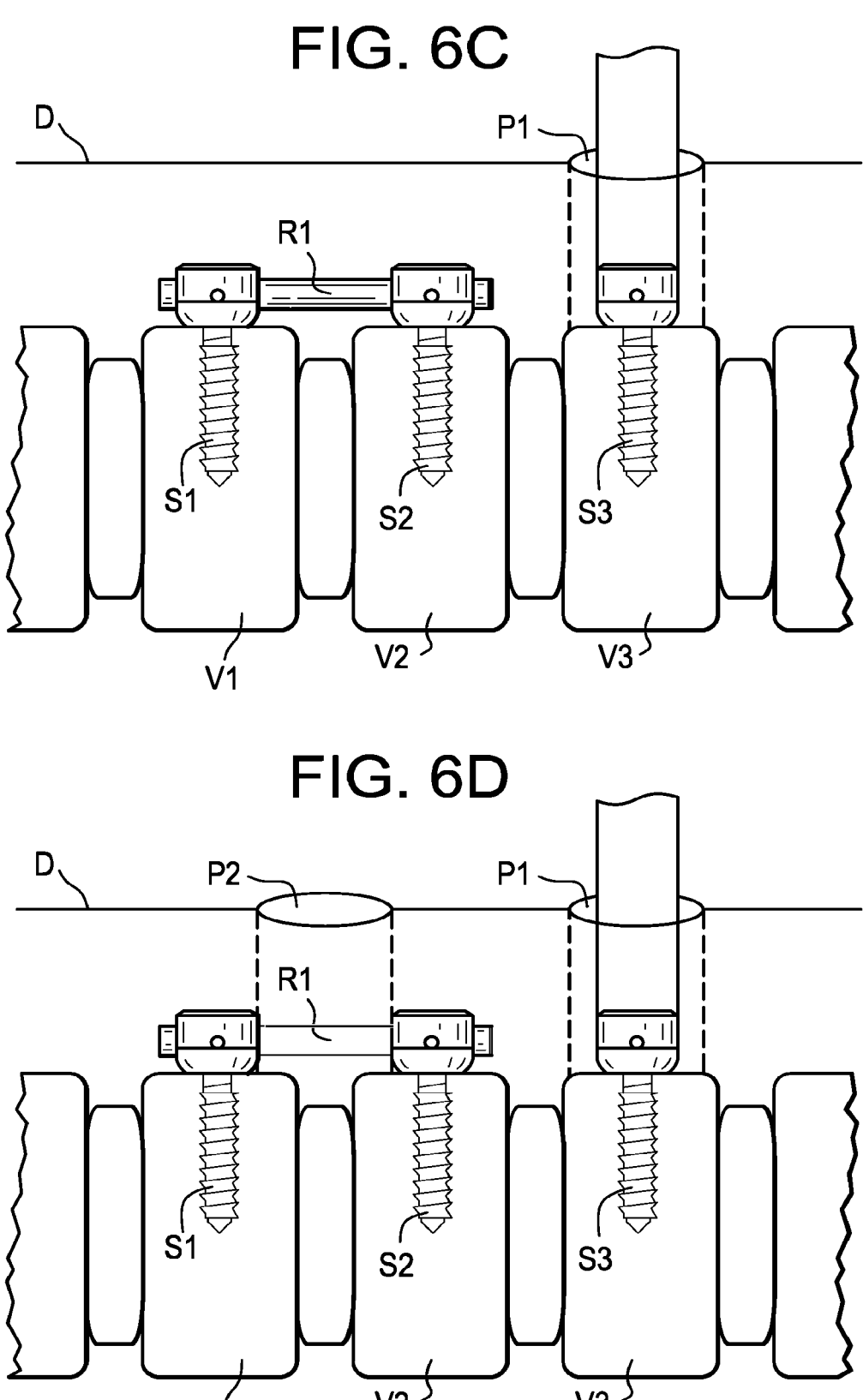

As shown in FIG. 6C, a pedicle screw S3 can be delivered through the minimally-invasive pathway P1 and can be implanted in the vertebra V3. Any of a variety of known techniques can be used to install the pedicle screw S3. For example, the screw S3 can be delivered over a guidewire docked in a pedicle of the vertebra V3 along a predetermined screw trajectory. The screw S3 can include one or more rod reduction tabs extending therefrom.

As shown in FIG. 6D, a second minimally-invasive pathway P2 can be formed to access a section of the rod R1 between the pedicle screws S1, S2. In some embodiments, a percutaneous access device can be used to provide the minimally-invasive pathway P2.

Figures 6E, 6F:
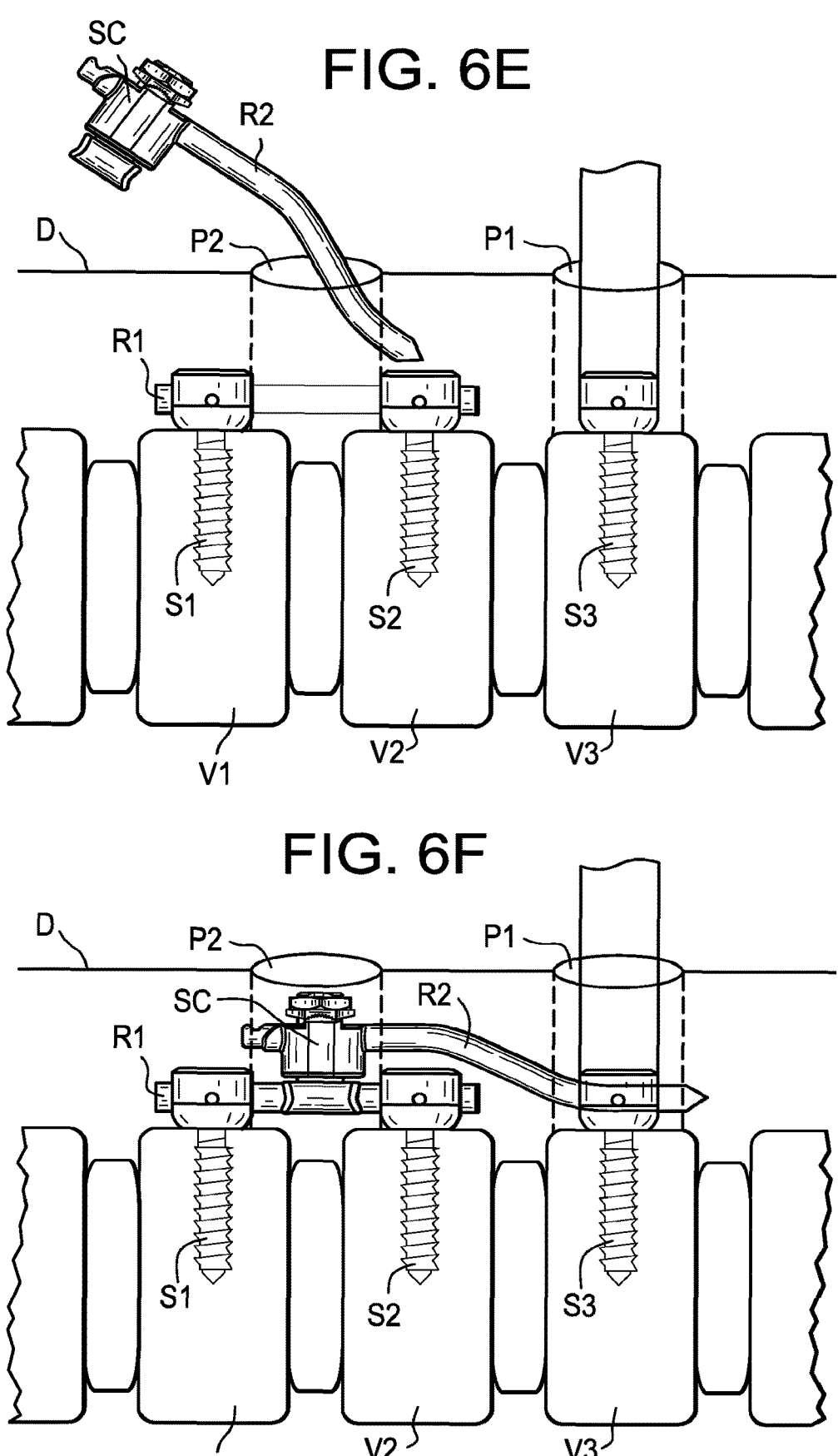

As shown in FIG. 6E, a spinal connector SC of the type described herein, including a spinal fixation element R2 thereof, can be passed through the second minimally-invasive pathway P2. The spinal connector SC can be advanced through the pathway P2, with a rounded or bulleted leading tip of the spinal fixation element R2 being tunneled subcutaneously through the rod-reduction tabs to position a portion of the spinal fixation element R2 within a rod-receiving recess of the pedicle screw S3.

As shown in FIG. 6F, a clamping portion or rod-receiving portion of the spinal connector SC can be coupled to the first spinal fixation element R1 at a position between the first and second pedicle screws S1, S2. One or more degrees of freedom of the spinal connector SC can be adjusted as needed to achieve the desired alignment. The spinal connector SC can be configured to provide tactile and/or audible feedback as described above (e.g., by "snapping" onto the spinal fixation element R1) to give the surgeon confidence that the connector is securely coupled to the spinal fixation element R1. Once the connector is in the desired position, or at any other appropriate time, a set screw or other locking element can be inserted through the first minimally-invasive pathway P1 to secure the spinal fixation element R2 to the pedicle screw S3. The set screw can also be preassembled with the pedicle screw S3 and then tightened once the connector and the spinal fixation element R2 are in the desired position. Before or after securing the spinal fixation element R2 to the pedicle screw S3, a driver or other instrument can be inserted through the second minimally-invasive pathway P2 to tighten or otherwise actuate a locking element of the spinal connector SC. As detailed above, a single locking element and a single actuation movement (e.g., rotation of a locking nut as shown) can be effective to cause the connector SC to clamp down on the spinal fixation element R1 and to lock any degrees of freedom of the spinal fixation element R2 with respect to the rest of the connector and, by extension, the spinal fixation element R1.

Figure 6G:
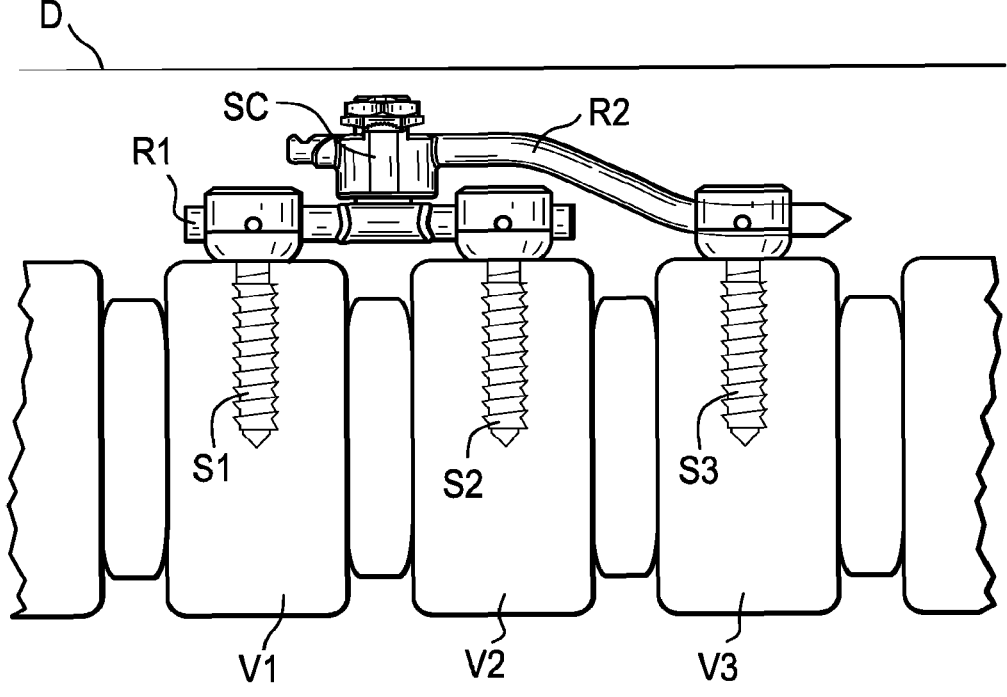

As shown in FIG. 6G the rod reduction tabs of the pedicle screw S3 can be removed and the first and second minimally-invasive pathways P1, P2 can be closed. The spinal connector SC can be left implanted in the patient to extend the previously-installed construct to an adjacent vertebral level as shown.

It should be noted that any ordering of method steps implied by the drawings or description herein is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present invention.

It will be appreciated that the spinal connectors disclosed herein can be used in any of a variety of methods that differ in one or more aspects from that described above. For example, the initially-placed construct need not be coupled to adjacent vertebrae, and need not be limited to only two vertebral levels as shown. By way of further example, an existing construct can be extended in a superior direction instead of an inferior direction as shown. As yet another example, an existing construct can be extended to a non-adjacent vertebra, and/or to more than one additional vertebra. While a procedure is shown with respect to a human spine, the connectors herein can be used to couple fixation elements to any bone, bones, or other structures in any living or non-living subject (e.g., humans, animals, machines, etc.). The above method need not necessarily be performed as part of a revision surgery with a previously-implanted construct, but rather can be used to extend a construct implanted as part of the same procedure in which the spinal connector is implanted. While pedicle screws and fixation rods are shown, it will be appreciated that various other hardware can be employed, such as bone hooks, wires, tethers, etc. and can be implanted in regions other than the pedicles. The method described above is not limited to use in minimally-invasive surgery, but rather can be used in open surgical procedures or in hybrid procedures.

While a spinal connector of the type shown in FIG. 5A is shown in the illustrated method, any of the spinal connectors disclosed herein can be used instead or in addition with any necessary modifications being apparent to one skilled in the art having read the above disclosure. For example, the connector 200 shown in FIG. 2A can be inserted through the minimally-invasive pathway P2, either before or after coupling the connector 200 to a rod R2 to be placed between the connector and the pedicle screw S3. By way of further example, the connector 100 shown in FIG. 1A, the connector 300 shown in FIG. 3A, or the connector 400 shown in FIG. 4A can be used in a manner similar to that shown.

In some embodiments, the rod R2 can be inserted first and then the spinal connector SC inserted subsequently. The various components of the spinal connector SC can be assembled entirely outside of the patient, entirely inside of the patient, or any combination thereof. In some embodiments, the rod R2 can be inserted in a direction opposite to that shown. For example, the rod R2 can be inserted through the pathway P1 and the leading end advanced subcutaneously in a superior direction into position adjacent the rod R1. The spinal connector SC can then be passed through the pathway P2 and used to couple the rods R1, R2 to one another. While bent or curved rods are shown, the rod can also be straight and pivoting polyaxial or uniplanar head of the screw S3 can be relied upon to clear the preexisting construct. In some embodiments, the rod R2 and the spinal connector SC can be implanted first and the screw S3 can be implanted thereafter. This can be the case particularly if the screw S3 is a side-loading screw. The spinal connector SC can be coupled to the rod R1 intermediate the screws S1, S2 as shown, or can be coupled to an end portion of the rod R1 that is not intermediate the screws S1, S2.

The spinal connectors disclosed herein can be formed from any of a variety of materials, such as nickel, titanium, stainless steel, polymers, ceramics, carbon fiber, etc. One or more components of the spinal connectors disclosed herein can be formed from a radiopaque material to facilitate visualization under fluoroscopy and other imaging techniques. Other components of the devices disclosed herein can be formed from a radiolucent material so as not to interfere with visualization of other components or bone structures.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. A connector, comprising:
a first spinal rod that extends along a length from a first end to a second end, the first spinal rod having a central opening formed thereon that is offset from the length at the first end thereof, the central opening defining a central longitudinal axis therethrough; and
a connection assembly having a clamp configured to receive a second spinal rod therein and a nut that engages the clamp to selectively lock an orientation of the first spinal rod relative to the connection assembly and an orientation of the connection assembly relative to the second spinal rod disposed within the clamp;
wherein the central opening is configured to rotatably couple the first spinal rod to the connection assembly, and wherein the second spinal rod is received in the clamp at a location that is collinear with the central longitudinal axis of the central opening.

2. The connector of claim 1, wherein the nut is configured to: (1) lock the position and orientation of the connector relative to the second spinal rod; and (2) lock first and second rotational degrees of freedom of the first spinal rod relative to the second spinal rod.

3. The connector of claim 1, wherein the clamp further comprises a proximally-protruding stud portion and a distally extending pair of opposed arms coupled to one another at a hinge portion.

4. The connector of claim 3, wherein each of the opposed arms includes an inner surface for mating to the second spinal rod.

5. The connector of claim 4, wherein the opposed arms are configured to be positionable between an unlocked configuration in which a slot formed between the arms has substantially parallel sidewalls and the clamp is movable with respect to the second spinal rod disposed between the inner surfaces of the arms and a locked configuration in which the opposed arms are deflected towards one another about the hinge portion and in which the second spinal rod disposed between the inner surfaces of the arms is locked to the clamp to resist or prevent rotation or sliding movement of the second spinal rod relative to the clamp.

6. The connector of claim 5, wherein the second spinal rod is disposed between the inner surfaces such that a longitudinal axis A3 of the second spinal rod extends perpendicular to a longitudinal axis of the stud portion and to a longitudinal axis along which the nut is advanced.

7. The connector of claim 3, wherein the stud portion further comprises a threaded surface on at least a portion thereof, the threaded surface being configured to threadably engage a corresponding thread formed on the nut to transition the connector between an unlocked configuration and a locked configuration.

8. The connector of claim 3, wherein the central opening is configured to receive at least a portion of the stud portion therethrough such that the central opening is rotatable about a central longitudinal axis of the stud portion until the nut is selectively locked.

9. The connector of claim 8, wherein the clamp is configured to be rotatable about a transverse axis A2 of the central opening.

10. The connector of claim 8, wherein the clamp is configured to be rotatable about a longitudinal axis A1 of the central opening.

11. The connector of claim 3, wherein the central opening is configured to allow positioning of the stud portion therein at a plurality of angles.

12. The connector of claim 11, wherein a longitudinal axis of the stud portion is collinear with the longitudinal axis of the central opening or the longitudinal axis of the stud portion extends at an oblique angle with respect to the longitudinal axis of the central opening.

13. The connector of claim 1, wherein the connection assembly further comprises a washer disposed between the clamp and the nut.

14. The connector of claim 13, wherein the central opening includes a lower surface configured to engage a shoulder formed on the clamp and an upper surface configured to engage the washer.

15. The connector of claim 14, wherein the upper surface includes first and second cylindrical protrusions with a plurality of teeth formed thereon that are configured to be engaged by corresponding surface features of the washer to lock a relative angle between the stud portion of the clamp and a ring-shaped structure formed integrally with the first spinal rod in which the central opening is defined about a transverse axis A2 of the central opening.

16. The connector of claim 1, wherein at least the first spinal rod is bendable.

17. A surgical method, comprising:
positioning a connector relative to a surgical site, the connector having:
at least a first spinal rod that extends from a first end to a second end, the first spinal rod having a central opening formed thereon that is offset from the length at the first end thereof, the central opening defining a central longitudinal axis therethrough; and
a clamp having an inner surface defined between a pair of opposed arms for mating to a second spinal rod therebetween at a location that is collinear with the central longitudinal axis of the central opening, and a nut;
positioning the second spinal rod between the inner surface;
rotating the first spinal rod to a desired position about one or more of a longitudinal axis A1 of a ring-shaped structure formed integrally with the first spinal rod in which the central opening is defined, or a transverse axis A2 of the ring-shaped structure; and
moving the clamp to a desired orientation with respect to the second spinal rod; and
engaging the clamp using the nut to selectively lock an orientation of the first spinal rod relative to the connector and an orientation of the connector relative to the second spinal rod disposed within the inner surface.

18. The method of claim 17, further comprising actuating the nut to: (1) lock the orientation of the connector relative to a second spinal rod; and (2) lock first and second rotational degrees of freedom of the first spinal rod relative to the second spinal rod.

19. The method of claim 18, wherein actuating the nut squeezes the ring-shaped structure of the first spinal rod into firm engagement with a shoulder of a stud portion that extends proximally from the clamp to resist or prevent the first spinal rod from rotating about the longitudinal axis A1 of the ring-shaped structure or the transverse axis A2 of the ring-shaped structure with respect to the stud portion.

20. The method of claim 19, further comprising retracting the nut proximally away from the shoulder to allow the arms to spread apart and move towards an unlocked configuration.

21. The method of claim 19, wherein the connector couples to the second spinal rod such that a longitudinal axis of the stud portion extends in an anterior-posterior direction relative to the surgical site in a patient.

22. The method of claim 19, wherein the connector couples to the second spinal rod such that a longitudinal axis of the stud portion extends in a medial-lateral direction relative to the surgical site in a patient.

23. The method of claim 17, wherein the second spinal rod comprises a previously-implanted spinal rod in the surgical site.

* * * * *